United States Patent
Hossain et al.

(10) Patent No.: US 11,547,983 B2
(45) Date of Patent: Jan. 10, 2023

(54) VANADIUM OXIDE CATALYSTS ON MIXED ALUMINA USEFUL FOR ALKANE TO ALKENE CONVERSION

(71) Applicant: KING FAHD UNIVERSITY OF PETROLEUM AND MINERALS, Dhahran (SA)

(72) Inventors: Mohammad Mozahar Hossain, Dhahran (SA); Idris Akolade Bakare, Dhahran (SA); Sagir Adamu, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 16/601,657

(22) Filed: Oct. 15, 2019

(65) Prior Publication Data

US 2022/0152594 A1    May 19, 2022

(51) Int. Cl.
*B01J 23/22* (2006.01)
*B01J 35/10* (2006.01)
(Continued)

(52) U.S. Cl.
CPC ............ *B01J 23/22* (2013.01); *B01J 23/02* (2013.01); *B01J 23/6482* (2013.01);
(Continued)

(58) Field of Classification Search
None
See application file for complete search history.

(56) References Cited

U.S. PATENT DOCUMENTS 9,815,752 B2   11/2017   Hossain et al.
9,878,305 B2    1/2018   Hossain et al.
(Continued)

FOREIGN PATENT DOCUMENTS

CN   1223170 A    7/1999
EP   0 790 225 A1  8/1997
KR   10-1951537 B1  2/2019

OTHER PUBLICATIONS

Xu et al. "Catalytic oxidative dehydrogenation of n-butane over V2/MO-Al2O3 [M=Mg, Ca, Sr, Ba] catalysts" Chinese Journal of Catalysis 36 (2015) 1060-1067. (Year: 2015).*
(Continued)

*Primary Examiner* — Philip Y Louie
*Assistant Examiner* — Alyssa L Cepluch
(74) *Attorney, Agent, or Firm* — Oblon, McClelland, Maier & Neustadt, L.L.P.

(57) ABSTRACT

Oxidative dehydrogenation (ODH) of alkanes to alkenes, e.g., propane to propylene, may use solid phase oxygen in $VO_x$ based mixed oxide catalysts. Beyond catalysis, the metal oxide species provide lattice oxygen. The catalysts can be prepared by depositing vanadium oxide(s) on $\theta\text{-}Al_2O_3$ mixed with various alkaline earth metal oxide support, e.g., CaO, MgO, BaO, etc. Surface area, acidity, and reduction properties of the catalyst systems can be modified by the support. The catalysts may allow multistage reduction of $VO_x$, indicating different $VO_x$ species. Vanadium on $\theta\text{-}Al_2O_3/CaO$ can suppress COx species, while vanadium on $\theta\text{-}Al_2O_3/BaO$ can yield at least ca. 49% olefins.

19 Claims, 16 Drawing Sheets

(51) Int. Cl.
  *B01J 23/02* (2006.01)
  *B01J 35/00* (2006.01)
  *B01J 21/04* (2006.01)
  *B01J 23/648* (2006.01)
  *B01J 27/232* (2006.01)
  *C07C 5/48* (2006.01)
  *C07C 11/06* (2006.01)

(52) U.S. Cl.
  CPC .......... *B01J 27/232* (2013.01); *B01J 35/002* (2013.01); *B01J 35/1014* (2013.01); *C07C 5/48* (2013.01); *B01J 21/04* (2013.01); *C07C 11/06* (2013.01)

(56) References Cited

U.S. PATENT DOCUMENTS

| | | | |
|---|---|---|---|
| 10,130,936 B2 | 11/2018 | Hossain et al. | |
| 2003/0166984 A1* | 9/2003 | Park | C07C 5/3332 585/444 |
| 2017/0354955 A1* | 12/2017 | Hossain | B01J 37/0203 |
| 2018/0044262 A1 | 2/2018 | Hossain et al. | |

OTHER PUBLICATIONS

Reddy et al. "Preparation, characterization, and activity of Al2O3-supported V2O5 catalysts" Journal of Catalysis 221 (2004) 93-101 (Year: 2004).*

Idris A. Bakare, et al., "Oxidative Dehydrogenation of Propane to Propylene over VO$_x$ on Mixed θ-Al$_2$O$_3$/Alkaline Earth Metal Oxide Supports", Industrials Engineering Chemistry Research, ACS Publications, May 29, 2019, 3 pages (Abstract only).

Zea Strassberger, et al., "Synthesis, characterization and testing of a new V$_2$O$_5$/Al$_2$O$_3$—MgO catalyst for butane dehydrogenation and limonene oxidation", Dalton Transactions, vol. 42, Feb. 21, 2013, pp. 5546-5553.

Afees A. Ayandiran, et al., "Oxidative dehydrogenation of propane to propylene over VO$_x$/CaO-γ-Al$_2$O$_3$ using lattice oxygen", Catalysis Science & Technology, Mar. 7, 2016, 14 pages.

N. Kraikul, et al., "Effects of Alumina Phase and Loading Amount of Catalytic Methane Combustion Activity of Pd- and Pt-Based Catalysts", Alche Annual Meeting, Conference Proceedings, Jan. 2004, pp. 8887-8897.

Ahmed I. Osman, et al., "Effect of precursor on the performance of alumina for the dehydration of methanol to dimethyl ether", Applied Catalysis B: Environmental, vol. 127, 2012, pp. 307-315.

Sameer Ali Al-Ghamdi, "Oxygen-Free Propane Oxidative Dehydrogenation Over Vanadium Oxide Catalysts: Reactivity and Kinetic Modelling", Electronic Thesis and Dissertation Repository, Dec. 2013, 270 pages.

* cited by examiner

VANADIUM OXIDE CATALYSTS ON MIXED ALUMINA USEFUL FOR ALKANE TO ALKENE CONVERSION

STATEMENT REGARDING PRIOR DISCLOSURES BY INVENTOR(S)

Aspects of the present disclosure are described in "Oxidative Dehydrogenation of Propane to Propylene over $VO_x$ on Mixed $\theta$-$Al_2O_3$/Alkaline Earth Metal Oxide Supports," which was authored by the inventors and published online in *Ind. Eng. Chem. Res.* 2019, 58(25), 10785-10792, on May 29, 2018, which is incorporated herein by reference in its entirety.

BACKGROUND OF THE INVENTION

Field of the Invention

The present disclosure relates to oxidative dehydrogenation (ODH) processes and the catalysis of such dehydrogenations, particularly with vanadium oxide catalysts on supports comprising $\theta$-$Al_2O_3$ and alkaline earth metal oxide(s), such as MgO, CaO, and/or BaO.

Description of the Related Art

Industrial demand for olefin compounds, particularly light olefins, has soared over the last decade, due to their functional position as key intermediates for the chemical industry. For example, the global production of ethylene and propylene, which are the most desirable light olefins have been estimated to be around 150 megatons of ethylene and 80 megatons of propylene per year. As part of ongoing efforts of the industries to meet this high demand, various technologies for olefins production have been developed in the art. Such olefin production methods include steam catalytic cracking, which accounts for approximately 70% of olefin production, paraffin dehydrogenation, and fluid catalytic cracking of naphtha. Further research advances in the technological field has led to the development of oxidative dehydrogenation (ODH) of light alkanes to olefins, which is an energy efficient process, utilizing a cost-effective catalyst with comparatively low carbon emissions.

The oxidative dehydrogenation (ODH) process has been considered superior to alternate techniques for olefin production due to fewer process downsides and advantages including low operating temperature, less coke formation (due to the presence of oxygen), and prolonged catalyst life time.

Although the oxidative dehydrogenation (ODH) of propane is postulated to be a favorable route for light olefin production, despite its inherent limitations such as low selectivity of propylene, coking, and formation of $CO_x$, which have limited the scale up of the process. In order to improve the selectivity for propylene, which is generally drastically decreased by propylene/propane re-combustion during the oxidative dehydrogenation (ODH) process, alternate reactor designs and catalyst development have been pursued.

Regarding developments of reactors to address these shortcomings, fluidized bed reactors have been found to offer some advantages over conventional reactor systems. Unlike conventional reactors, fluidized bed reactors can offer more uniform residence time distribution, elimination of mass transfer limitations, and controlled isothermal conditions. For example, hot spots in fixed bed reactors may be avoided with fluidized bed reactors. In addition, the periodic re-oxidation of the catalyst using the twin reactor system, i.e., reaction and catalyst regeneration, offered by certain fluidized bed reactor designs can further ease the operation of oxidative dehydrogenation (ODH) and other technologies on an industrial level.

Oxidative dehydrogenation (ODH) processes most frequently employ vanadium supported catalysts and molybdenum supported catalysts. Of these, vanadium-based catalysts are the most widely used due to a characteristic lattice oxygen that enhances the dehydrogenation of alkanes.

U.S. Pat. Nos. 9,878,305 and 10,130,936 to Hossain et al. (Hossain) disclose fluidizable catalysts for gas phase oxygen-free oxidative dehydrogenation of alkanes, such as propane, to corresponding olefins, such as propylene. Hossain's catalysts have 5 to 20 wt. % of total catalyst weight of one or more vanadium oxides ($VO_x$), such as $V_2O_5$. Hossain's dehydrogenation catalysts are disposed on an alumina support that is modified with calcium oxide to influence characteristics of lattice oxygen at the catalyst surface. Hossain describes improved alkane conversion and olefin product selectivity are also disclosed, but only generically describes alumina, and specifically describes $\gamma$-$Al_2O_3$, modified by calcium oxide.

CN 1223170 A by Yu (Yu) discloses a catalyst composition for preparing olefins by dehydrogenation of alkane, made up one vanadium compound and Li, K, Cs, Ba, Ca, Mg, Sn, Mo, Ti, Zr, Zn, Cu, Ag, La, Nd, Pr, and/or Ce compound, loaded on $\gamma$-alumina carrier vy drying and calcining. Yu's catalyst has no carcinogenic chromium or noble metal(s) and is useable in fluidized-bed, moving-bed, or fixed-bed reactors. Yu's catalyst uses from 10 to 30 wt. % $\gamma$-alumina (and no other form of alumina), relative to total catalyst weight and has a specific surface area of 100 to 1000 $m^2/g$, preferably 300 to 800 $m^2/g$.

EP 0 790 225 A1 by Niemi (Niemi) discloses a process and catalyst for alkane dehydrogenation, wherein the alkanes are contacted at an elevated temperature with a vanadium-containing catalyst in order to prepare alkenes. Before Niemi's dehydrogenation reaction Niemi's catalyst is reduced with carbon monoxide, which improves the activity and selectivity of the catalyst. Niemi's catalyst may contain modification metals, for example calcium or zirconium. Niemi recommends vanadium in 1 to 15 wt. %, particularly 2 to 5 wt. %, calculated as vanadium metal, of the weight of the catalyst. Niemi's support may be any available support, particularly, $\gamma$, $\theta$, or $\delta$-aluminum oxide, having a surface area of 50 to 400 $m^2/g$. Niemi modifies its catalyst metal with alkaline-earth metals, in particular calcium and strontium, or elements of Group IV A, in particular zirconium, whereby the molar ratio of vanadium to alkaline-earth metal should be below 4. Niemi does not mention the presence of oxides and carbonates of alkaline earth metals on the vanadium-containing catalyst.

KR 10-1951537 B1 by Yeom et al. (Yeom) discloses a composite catalyst carrier with a carrier having a mesopore of 5 to 50 nm and macropores of 50 nm to 20 μm, doped with a mixture of MgO or Mg—Sn oxide. Yeom's carrier may be alumina and/or silica, but preferably 90% or more $\theta$-alumina. Yeom's catalyst uses a transition metal active ingredient such Pt, Pd, Ni, Co, Ru, Re, Rh, Os, Ti, V, Cr, Mn, Fe, Cu, and/or Zn, but does not clearly disclose vanadium oxides and requires a bimodal pore distribution.

*Dalton Trans.* 2013, 42, 5546-5553 by Strassberger et al. (Strassberger) discloses $V_2O_5$/$Al_2O_3$—MgO catalysts for oxidative dehydrogenation and epoxidation reactions. Strassberger's catalyst is anchored via an exchange reaction between the vanadium complex and surface hydroxyl groups, to give monomeric vanadium species at 5 wt. % $V_2O_5$ loading, along with polymeric species at 5 and 10 wt % $V_2O_5$ loadings. Strassberger obtains butenes and 1,3-butadiene in moderate selectivity at 8 to 10% conversion by dehydrogenation, and epoxidizes limonene in 50 to 70% selectivity to the 1,2-epoxide at 10 to 20% conversion. Strassberger's catalysts have BET surface areas of at least 140 m$^4$/g and pore volumes of at least 0.30 cm$^3$/g, wherein the support was 40:60 $Al_2O_3$—MgO.

The doctoral thesis entitled "Oxygen-free Propane Oxidative Denydrogenation Over Vanadium Oxide Catalysts: Reactivity and Kinetic Modelling," by Sameer A. Al-Ghamdi in the Graduate Program in Engineering Science Department of Chemical and Biochemical Engineering Faculty of Engineering Science of the University of Western Ontario, London, Ontario) in 2013 (Al-Ghamdi) discloses propane conversion to propylene by oxidative dehydrogenation (ODH) with vanadium oxide catalysts suitable for fluidized-bed reactors and the structure-reactivity relationship of VO), catalysts using the lattice oxygen of vanadium oxide catalysts in the absence of gas-phase oxygen. Al-Ghamdi describes 5-10 wt. % $VO_x$ catalysts on γ-$Al_2O_3$, reporting that monomeric $VO_x$ species predominate at low V loadings while polymeric $VO_x$ species increase with higher loadings until monolayer surface coverage is reached. Al-Ghamdi describes propane conversions of 12 to 15% in ODH experiments in the CREC Riser Simulator over partially reduced catalyst and propylene selectivities of 68 to 86% at 475 to 550° C. Al-Ghamdi does not use θ-$Al_2O_3$ in its catalyst, and the BET surface areas of the vanadium on γ-alumina catalysts described therein are above 150 m$^2$/g.

As explained in *Appl. Catalysis B: Environm.* 2012, 127, 307-315, and the 2004 AIChE Annual Topics in Fuel Cell Technology Meeting paper entitled "Effects of Alumina Phase and Loading Amount on Catalytic Methane Combustion Activity of Pd- and Pt-Based Catalysts," by Kraikul et al., both incorporated herein by reference, the phase of alumina has substantial and unpredictable effects on catalyst performance.

As explained in "Synthesis of Different Crystallographic $Al_2O_3$Nanomaterials from Solid Waste for Application in Dye Degradation", RSC Adv., 2014, 4, 50801. DOI: 10.1039/c4ra08842e by Singh et al., the choice of alumina phase leads to unpredictable effects on catalyst chemistry, structure and/or catalytic behavior.

In light of the above, a need remains for catalyst systems for the oxidative dehydrogenation of alkanes to alkenes, particularly for ethane, propane, and butane to ethylene, propylene, 1-butene, and isobutylene, such as vanadium oxide catalysts on supports of particular alumina and alkaline earth metal combinations, and methods of making and using such catalysts in olefin generation.

SUMMARY OF THE INVENTION

Aspects of the invention provide catalysts comprising: at least 65 wt. %, based on total catalyst weight, of a support material comprising, based on total support weight, at least 50 wt. % θ-alumina, at least 5 wt. % of an alkaline earth metal oxide, and at least 5 wt. % of an alkaline earth metal carbonate; and 5 to 20 wt. %, based on the total catalyst weight, of a catalytic material comprising at least 90 wt. %, based on total catalytic material weight, of one or more vanadium oxides, disposed on the support material, wherein the alkaline earth metal oxide is present in the alumina in a weight percentage in a range of from 5 to 60 wt. %.

Inventive catalysts may be modified by any permutation of the features described herein, particularly the following.

The alkaline earth metal oxide may comprise magnesium oxide, calcium oxide, strontium oxide, and/or barium oxide. The alkaline earth metal carbonate may comprise magnesium carbonate, calcium carbonate, strontium carbonate, and/or barium carbonate.

The alkaline earth metal oxide may comprise at least 90 wt. % calcium oxide, based on total alkaline earth metal oxide weight, and/or the alkaline earth metal carbonate may comprise at least 90 wt. % calcium carbonate.

The alkaline earth metal oxide may comprise at least 90 wt. % barium oxide, based on total alkaline earth metal oxide weight, and/or the alkaline earth metal carbonate may comprise at least 90 wt. % barium carbonate.

The vanadium oxide(s) may comprise an amount in a range of from 5 to 50 wt. % of $V_2O_5$, relative to total vanadium oxide weight. The support material may comprise at least 25 wt. % of the alkaline earth metal carbonate. The catalytic material may be up to 10 wt. % of the total catalyst weight, with a remainder of the catalyst weight being the support material.

Inventive catalysts may have a BET surface area in a range of from 15 to 60 m$^2$/g. Inventive catalysts may have a total acidity in a range of 0.6 to 1.5 mmol of $NH_3$ per gram of catalyst.

Inventive catalysts may be suitable to provide a higher olefin selectivity in oxidative dehydrogenation absent gaseous oxygen at 625° C. relative to 600 and 650° C. Inventive catalysts may be suitable to provide a higher olefin yield in oxidative dehydrogenation absent gaseous oxygen at 625° C. relative to 600 and 650° C. Inventive catalysts may be suitable to provide an olefin selectivity over 40% in oxidative dehydrogenation absent gaseous oxygen at 625° C. Inventive catalysts may be suitable to provide an olefin yield over 30% in oxidative dehydrogenation absent gaseous oxygen at 625° C. Inventive catalysts may be suitable to provide a selectivity to $CO_x$ of no more than 5% in oxidative dehydrogenation absent gaseous oxygen at 625° C.

Aspects of the invention provide methods for dehydrogenating an alkane to a corresponding olefin, which methods may comprise: flowing a stream comprising the alkane through a reaction space of a fluidized bed reactor comprising any permutation of inventive catalyst(s) described herein at a temperature in a range of 500 to 700° C., thereby forming the corresponding olefin, wherein the dehydrogenating is performed in an environment free of gaseous oxygen.

Such methods may employ an alkaline earth metal oxide of the catalysts comprising at least 90 wt. % barium oxide, based on total alkaline earth metal oxide weight, an alkaline earth metal carbonate comprising at least 90 wt. % barium carbonate, and/or catalyst(s) having a BET surface area no greater than 50 m$^2$/g. Such methods may employ an alkaline earth metal oxide of the catalysts comprising at least 90 wt. % calcium oxide, based on total alkaline earth metal oxide weight, an alkaline earth metal carbonate comprising at least 90 wt. % calcium carbonate, and/or catalyst(s) having a BET surface area no greater than 50 m$^2$/g.

Inventive methods may be ones in which the alkane is propane, and the propane conversion is in a range of from 60 to 98%. Inventive methods may be ones in which the alkane is propane, the corresponding olefin is propylene, and the propylene selectivity is in a range of from 20 to 60%.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
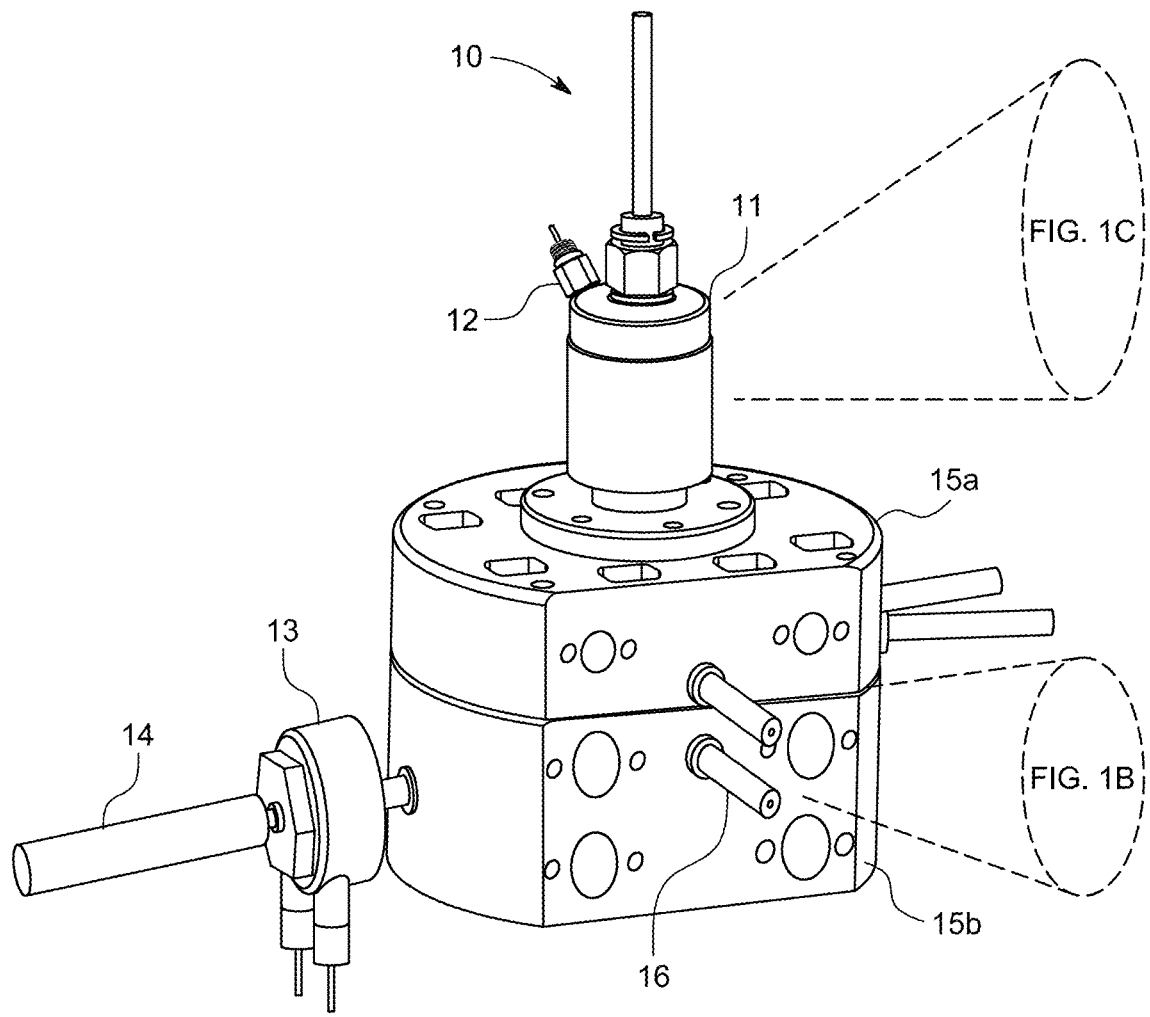
FIG. 1A shows a grayscale representative sketch of a portion of the riser simulator, including the upper and lower reactor, used to model the oxidative dehydrogenation (ODH) reactions described herein.
Figure 1B:
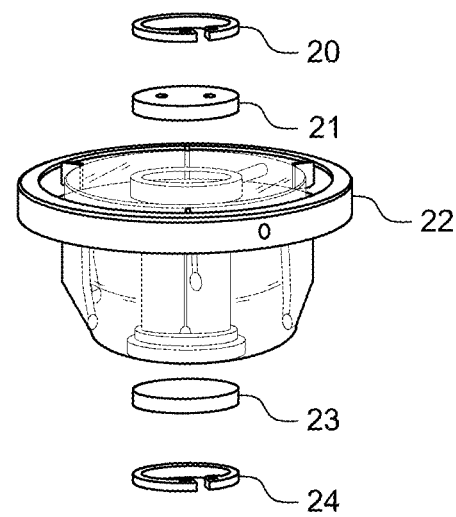
FIG. 1B shows a representative sketch of a portion the riser simulator, including the impeller in closer detail.
Figure 1C:
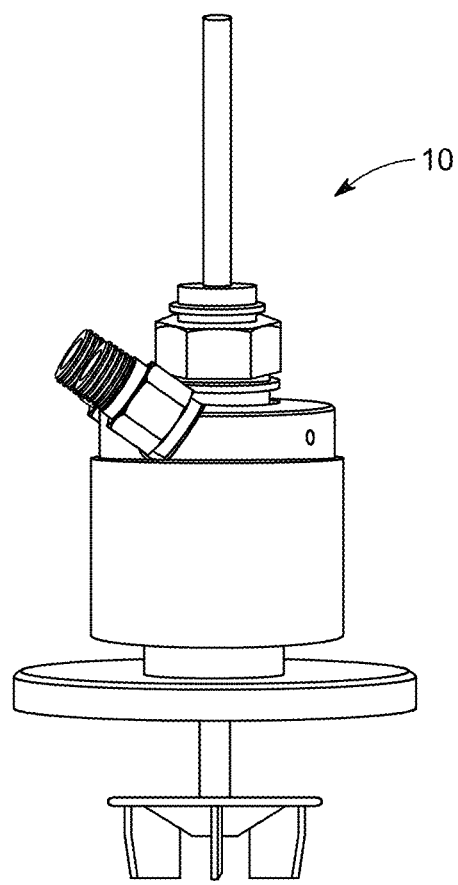
FIG. 1C shows a representative sketch of a portion the riser simulator, including the catalyst basket components in closer detail.
Figure 1D:
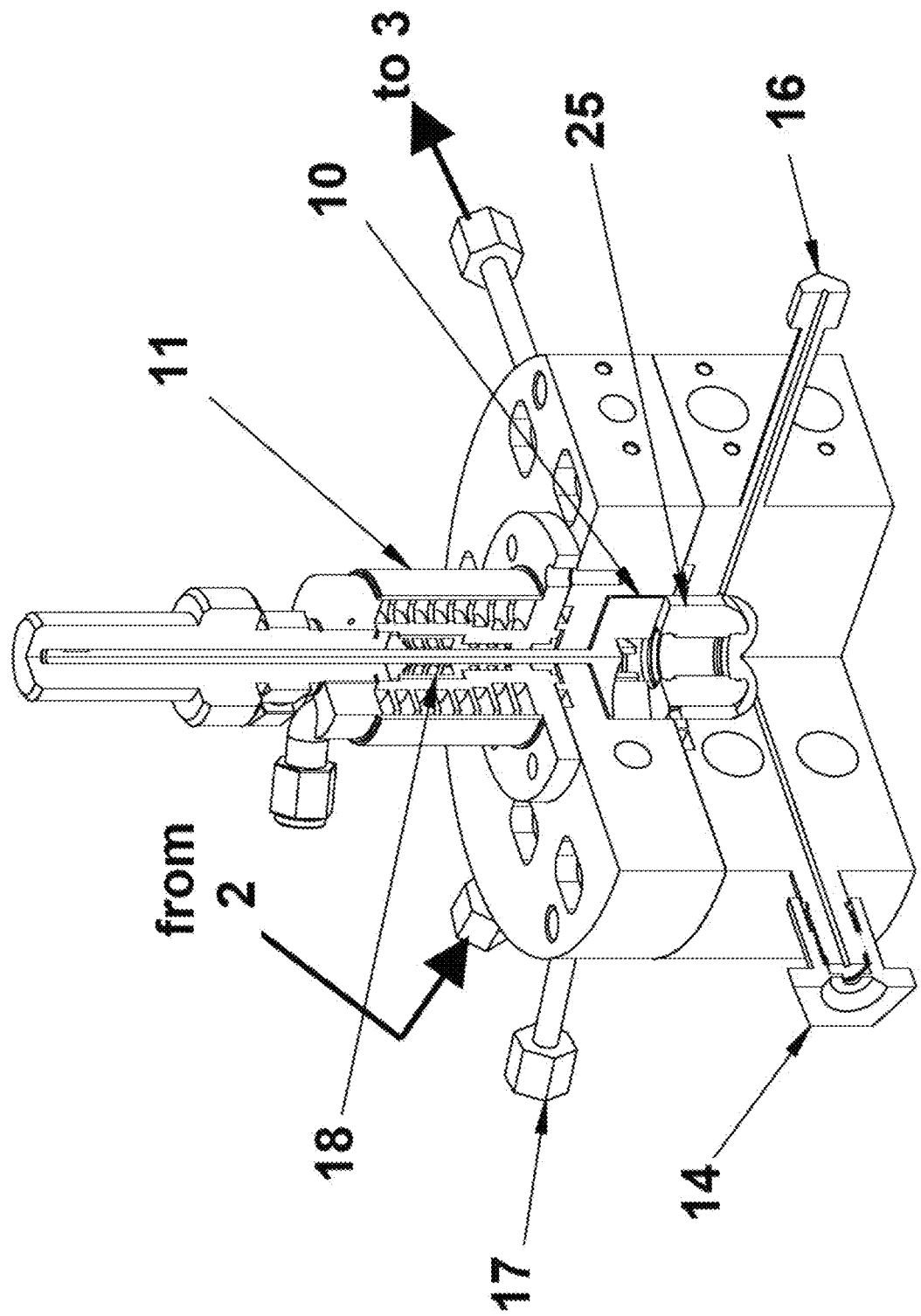
FIG. 1D shows a representative sketch of a portion, including the upper and lower reactor spaces, used to model the oxidative dehydrogenation (ODH) reactions described herein.

Aspects of the invention provide catalysts comprising: at least 65, 70, 75, 80, 85, 90, or 95 wt. %, based on total catalyst weight, of a support material comprising, based on total support weight, at least 33, 40, 45, 47.5, 50, 52.5, 55, 60, 65, or 70 wt. % $\theta$-alumina, at least 5, 5.5, 6, 6.5, 7, 7.5, 8, 8.5, 9, 9.5, 10, 12.5, 15, 17.5, 20, 22.5, 25, 30, 35, 40, 45, or 50 wt. % (and/or up to 70, 65, 60, 55, 50, 45, 40, 35, 30, 27.5, 25, 22.5, 20, 17.5, or 15 wt. %) of an alkaline earth metal oxide, particularly magnesium oxide, calcium oxide, strontium oxide, and/or barium oxide, and at least 5, 7.5, 10, 12.5, 15, 17.5, 20, 25, 30, 35, 40, or 45 wt. % (and/or 50, 47.5, 45, 42.5, 40, 37.5, 35, 32.5, 30, 27.5, 25, 22.5, 20, 17.5, or 15 wt. %) of an alkaline earth metal carbonate, particularly magnesium carbonate, calcium carbonate, strontium carbonate, and/or barium carbonate; and 5 to 20 wt. %, e.g., at least 5, 5.5, 6, 6.5, 7, 7.5, 8, 8.5, 9, 10, 11, 12.5, or 15 wt. % and/or up to 20, 19, 18, 17.5, 17, 16, 15, 14, 13, 12.5, 12, 11, 10, 9.5, 9, 8.5, 8, 7.5, or 7 wt. %) based on the total catalyst weight, of a catalytic material comprising at least 90, 91, 92, 92.5, 93, 94, 95, 96, 97, 97.5, 98, 99, 99.1, 99.5, or 99.9 wt. %, based on total catalytic material weight, of one or more vanadium oxides, $VO_3$, $VO_4$, and/or $V_2O_5$, etc., disposed on the support material, wherein the alkaline earth metal oxide is present in the alumina in a weight percentage in a range of from 5 to 60 wt. %, e.g., at least 5, 6, 7, 8, 9, 10, 11, 12, 13, 14, 15, 17.5, or 20 wt. % and/or up to 60, 55, 50, 45, 40, 35, 30, 27.5, 25, 22.5, 20, 17.5 or 15 wt. %.

The alkaline earth metal oxide may comprise at least 90, 91, 92, 92.5, 93, 94, 95, 96, 97, 97.5, 98, 99, 99.1, 99.5, or 99.9 wt. % calcium oxide, based on total alkaline earth metal oxide weight, and/or the alkaline earth metal carbonate may comprise at least 90, 91, 92, 92.5, 93, 94, 95, 96, 97, 97.5, 98, 99, 99.1, 99.5, or 99.9 wt. % calcium carbonate.

The alkaline earth metal oxide may comprise at least 90, 91, 92, 92.5, 93, 94, 95, 96, 97, 97.5, 98, 99, 99.1, 99.5, or 99.9 wt. % barium oxide, based on total alkaline earth metal oxide weight, and/or the alkaline earth metal carbonate may comprise at least 90, 91, 92, 92.5, 93, 94, 95, 96, 97, 97.5, 98, 99, 99.1, 99.5, or 99.9 wt. % barium carbonate.

The vanadium oxide(s) may comprise an amount in a range of from 5 to 50 wt. % of $V_2O_5$, relative to total vanadium oxide weight, e.g., at least 5, 6, 7, 8, 9, 10, 11, 12, 12.5, 13, 14, 15, 17.5, or 20 wt. % and/or up to 50, 47.5, 45, 42.5, 40, 37.5, 35, 32.5, 30, 27.5, 25, 22.5, 20, 17.5, 15, or 12.5 wt. % $V_2O_5$.

The support material may comprise at least 25 wt. % of the alkaline earth metal carbonate, e.g., at least 25, 26, 27, 27.5, 28, 29, 30, 32.5, 35, 37.5, 40, 42.5, 45, 47.5, or 50 wt. % and/or up to 70, 65, 60, 57.5, 55, 52.5, 50, 47.5, 45, 42.5, 40, 37.5, 35, 32.5, or 30 wt. % magnesium carbonate, calcium carbonate, strontium carbonate, and/or barium carbonate, individually or in combination.

The catalytic material may be up to 15, 14, 13, 12.5, 12, 11, 10, 9.5, 9, 8.5, 8, 7.5, 7, 6.5, 6, or 5 wt. % of the total catalyst weight, with a remainder of the catalyst weight being the support material and optionally further substantially inert components, i.e., which do not alter the conversion at 625° C. in ODH by any more than 5, 4, 3, 2.5, 2, or 1%.

Inventive catalysts may have a BET surface area in a range of from 15 to 60 m$^2$/g, e.g., at least 15, 16, 17.5, 18, 19, 20, 22.5, 25, 27.5, 30, 32.5, or 35 m$^2$/g and/or up to 60, 57.5, 55, 52.5, 50, 47.5, 45, 42.5, 40, 37.5, 35, 32.5, 30, 27.5, 25, 22.5, 20, 17.5, or 15 m$^2$/g.

Inventive catalysts may have a total acidity in a range of 0.6 to 1.5 mmol of $NH_3$ per gram of catalyst, e.g., at least 0.55, 0.6, 0.65, 0.675, 0.7, 0.725, 0.75, 0.775, 0.8, 0.825, 0.85, 0.875, 0.9, 0.925, 0.95, 0.975, 1.0, 1.025, 1.05, 1.075, or 1.1 mmol $NH_3$/g and/or up to 1.25, 1.225, 1.2, 1.175, 1.15. 1.125, 1.1, 1.075, 1.05. 1.025, 1.0, 0.975, 0.95, 0.925, 0.9, 0.875, 0.85, 0.825, 0.8, 0.775, or 0.75 mmol $NH_3$/g. The acidity of inventive catalysts is generally temperature dependent, but may be tailored to increase or decrease with temperature, e.g., 0.01, 0.1, 0.25, 0.5, 0.75, 1, 1.5, 2, 2.5, 3, 3.5, 4, 5, 6, 7, 7.5, 10, 12.5, or 15% per ° C. For example, certain arrangements doping with calcium, strontium, and/or barium oxide(s) and/or carbonate(s), the acidity of inventive catalysts and/or support materials may decrease with increasing temperature, while arrangements doping with calcium and/or beryllium oxide(s) and/or carbonate(s) may cause the acidity of inventive catalysts and/or support materials to increase with increasing temperature.

Inventive catalysts may be suitable to provide a higher olefin selectivity and/or higher olefin yield in oxidative dehydrogenation absent gaseous oxygen at 625° C. relative to 600 and 650° C., e.g., 1, 2, 3, 4, 5, 7.5, 10, 12.5, 15, 17.5, 20, 25, or 33% higher, e.g., with Ca, Sr, and/or Ba. Inventive catalysts may alternatively be suitable to provide a lower olefin selectivity and/or lower olefin yield in oxidative dehydrogenation absent gaseous oxygen at 625° C. relative to 600 and 650° C., e.g., with Mg and/or Be.

Inventive catalysts may be suitable to provide an olefin selectivity over 40, 41, 42, 42.5, 43, 44, 45, 46, 47, 47.5, 48, 49, 50, 52.5, 55% or more (e.g., up to 65, 62.5, 60, 57.5, 55, 52.5, 50, 47.5, or 45%) in oxidative dehydrogenation absent gaseous oxygen at 625° C. Inventive catalysts may be suitable to provide an olefin yield over 30, 31, 32, 32.5, 33, 34, 35, 36, 37, 37.5, 38, 39, 40, 42.5, 45, 47.5, 50, 52.5, 55% or more (e.g., up to 70, 67.5, 65, 62.5, 60, 57.5, 55, 52.5, 50, 47.5, 45, 42.5, or 40%) in oxidative dehydrogenation absent gaseous oxygen at 625° C.

Inventive catalysts may be suitable to provide a selectivity to $CO_x$ of no more than 5, 4, 3, 2.5, 2, 1, 0.5, 0.1, 0.01% in oxidative dehydrogenation absent gaseous oxygen at 625° C.

Aspects of the invention provide methods for dehydrogenating an alkane to a corresponding olefin, which methods may comprise: flowing a stream comprising the alkane through a reaction space of a fluidized bed reactor comprising any permutation of inventive catalyst(s) described herein at a temperature in a range of 500 to 700° C., e.g., at least 500, 510, 525, 550, 575, 600, 625, or 650° C. and/or up to 700, 675, 650, 625, or 600° C., thereby forming the corresponding olefin, wherein the dehydrogenating is performed in an environment free of gaseous oxygen, such as $O_2$, air, or the like. Relevant alkanes may include molecules comprising 2, 3, 4, 5, 6, 7, 8, 9, 10, 11, 12, 13, 14, 15, 16, or more carbon atoms, of which at least two of the carbon atoms are adjacent aliphatic carbons, or arranged such that a cumulation or conjugation can arise from ODH, e.g., ethane, propane, n-butane, isobutane, n-pentane, isopentane, cyclopentane, n-hexane, isohexane, 2,3-dimethylbutane, 3-methylpentane, cyclohexane, 2,2-dimethylbutane, n-heptane, isoheptane, methylcyclohexane, 3,3-dimethylpentane, 2,3-dimethylpentane, 2,4-dimethylpentane, etc. Corresponding alkenes may be the particular alkane with two adjacent (non-geminal) hydrogens removed across a carbon bond, i.e., ethylene from ethan, propylene from propane, isobutene from isobutane (or n-butane), 1-butene from n-butane, etc.

Such methods may employ an alkaline earth metal oxide of the catalysts comprising at least 90, 91, 92, 92.5, 93, 94, 95, 96, 97, 97.5, 98, 99, 99.1, 99.5, 99.9, or 99.99 wt. % calcium oxide and/or barium oxide (e.g., a remainder being the other of CaO or BaO and any inevitable alkaline earth metal oxides), based on total alkaline earth metal oxide weight, an alkaline earth metal carbonate comprising at least 90, 91, 92, 92.5, 93, 94, 95, 96, 97, 97.5, 98, 99, 99.1, 99.5, 99.9, or 99.99 wt. % calcium carbonate and/or barium oxide (e.g., a remainder being the other of CaO or BaO and any inevitable alkaline earth metal carbonates), and/or catalyst(s) having a BET surface area no greater than 50, 48, 46, 45, 44, 42.5, 41, 40, 39, 38, 37, 36, 35, 34, 33, 32, 31, 30, 29, 28, 27, 26, 25, 24, 23, 22, 21, 20, or 19 m²/g. The support materials may consist essentially of the alumina (preferably at least 75, 80, 85, 90, 91, 92, 92.5, 93, 94, 95, 96, 97, 97.5, 98, 99, 99.1, 99.5, or 99.9% in θ-form) and the alkaline earth metal oxide(s) and/or carbonate(s).

Inventive methods may be ones in which the alkane is propane, and the propane conversion is in a range of from 60 to 98%, e.g., at least 60, 62.5, 65, 67.5, 70, 72.5, 75, 76, 77, 78, 79, or 80% and/or up to 98, 97, 96, 95, 94, 93, 92, 91, or 90%. Likewise, the alkane may include ethane, propane, n-butane, and/or isobutane (including gas mixtures).

Inventive methods may be ones in which the alkane is propane, the corresponding olefin is propylene, and the propylene selectivity is in a range of from 20 to 60%, e.g., at least 20, 22.5, 25, 27.5, 30, 32.5, 35, 37.5, 40, 41, 42, 43, 44, and/or 45% and/or up to 60, 59, 58, 57, 56, 55, 54, 53, 52, 51, or 50%. Likewise, the alkane may include ethane, propane, n-butane, and/or isobutane (including gas mixtures, or course).

Aspects of the invention may exclude γ-alumina, δ-alumina, and/or all types of alumina besides θ-alumina, or no more than 40, 33, 25, 20, 15, 10, 7.5, 5, 4, 3, 2, 1, 0.5, or 0.1 wt. %, relative to the total alumina weight, of non-θ-alumina(s), such as γ-alumina, δ-alumina, etc., individually or in combination.

Aspects of the invention may employ trace noble metals, such as Au, Ag, Pd, and/or Pt, but generally do not require these, and may contain no more than 5, 4, 3, 2.5, 2, 1, 0.5, 0.1, 0.01, 0.001, 0.0001, or 0.00001 wt. % relative to total elemental catalytic metal weight, of any noble metals, individually or in combination, or at least 1 ppb thereof.

Aspects of the invention may exclude or include no more than trace Ta, Nb, and/or lanthanide(s), La, Ce, Pr, Nd, Pm, Sm, Eu, Gd, Tb, Dy, Ho, Er, Tm, Yb, and/or Lu, or may comprise no more than 2.5, 2, 1, 0.75, 0.5, 0.25, 0.1, 0.01, 0.001, 0.0001, 0.00001, or 0.000001 wt. %, relative to total catalyst weight, of tin, niobium, and/or lanthanide(s), individually or in combination.

Aspects of the invention may exclude or include no more than trace Mo, Ti, Sn, Zr, Zn, Cu, Pt, Pd, Au, and/or Ag, or may comprise no more than 5, 4, 3 2.5, 2, 1, 0.75, 0.5, 0.25, 0.1, 0.01, 0.001, 0.0001, or 0.00001 wt. %, relative to total catalyst weight, of Mo, Ti, Sn, Zr, Zn, Cu, and/or Ag, individually or in combination.

Aspects of the invention comprise oxidative dehydrogenation (ODH) reactions of alkanes, such as ethane or propane, using $VO_x$ supported on CaO/θ-$Al_2O_3$, MgO/θ-$Al_2O_3$, and/or BaO/θ-$Al_2O_3$. Aspects of the invention diminish the inclination of θ-$Al_2O_3$ to favor the over-oxidation of reactant to $CO_x$ species and coke, mixing acidic θ-$Al_2O_3$ and basic support, such as BaO, CaO, and/or MgO, in catalyst systems with mild acidic properties that may reduce such over-oxidation of reactants. Aspects of the invention include synergic effects of combining θ-$Al_2O_3$, CaO, MgO, and/or BaO, and/or provide overall more stable and durable catalyst systems. Aspects of the invention employ wet impregnation to synthesis inventive catalysts. Inventive catalytic oxidative dehydrogenations of alkanes, such as propane, may be carried out in using a fluidized or other reactor in absence of gas phase oxygen. Aspects of the invention include the oxidative dehydrogenation (ODH) of propane with the solid phase oxygen of the catalysts, generally attaining higher propylene yields by a proper control of the catalyst acidity and oxygen carrying capacity.

Aspects of the invention provide improved catalysts for propylene production via the oxidative dehydrogenation (ODH) of propane. All inventive samples described in more detail below show good activity in the oxidative dehydrogenation (ODH) of propane. In particular, exemplary $VO_x$ on $\theta$-$Al_2O_3$/CaO (VC) and $VO_x$ on $\theta$-$Al_2O_3$/BaO (VB) samples show better selectivity for producing propylene compared to $VO_x$ on $\theta$-$Al_2O_3$ (V) and $VO_x$ on $\theta$-$Al_2O_3$/MgO (VM).

Aspects of the invention, through the presence of MgO, CaO, and/or BaO can decrease the specific surface area of the catalysts, e.g., down to 65, 62.5, 60, 57.5, 55, 52.5, 50, 49, 48, 47.5, 47, 46, or 45 $m^2/g$ for MgO-modified catalysts, down to 50, 47.5, 45, 44, 43, 42.5, 42, 41, 40, 39.5, 39, 38.5, 38, 37.5, or 37 $m^2/g$ CaO-modified catalysts, and down to 27.5, 25, 24, 23, 22.5, 22, 21, 20, 19.5, 19, 18.5, 18, 17.5, or 17 $m^2/g$ for BaO-modified catalysts, ostensibly due to increased atomic radius of the alkaline earth metal oxide. Incorporating MgO, CaO, and/or BaO into the catalyst systems can provide ODH catalysts with mild acidic properties which can regulate over-oxidation of reactants to COx and/or suppress coke formation.

X-ray diffraction (XRD) and x-ray photoelectron spectroscopy (XPS) analyses indicate that inventive forms $VO_x$ on $\theta$-$Al_2O_3$/BaO (VB) and $VO_x$ on $\theta$-$Al_2O_3$/CaO (VC) may contain some carbonate forms, which may derive from acetate moieties in the vanadium precursor. Carbonate in $VO_x$ on $\theta$-$Al_2O_3$/BaO (VB), for example, as well as other catalysts, can be stable beyond the calcination temperature of 550° C. Carbonate formation may contributed to distinctive properties of the $VO_x$ on $\theta$-$Al_2O_3$/BaO (VB) and $VO_x$ on $\theta$-$Al_2O_3$/CaO (VC) exemplary catalysts, compared to $VO_x$ on $\theta$-$Al_2O_3$/MgO (VM).

Unmodified $VO_x$ on $\theta$-$Al_2O_3$ catalysts may show increased in propane conversion by raising the temperature from 600 to 625° C., i.e., from 57 to 86%. The increased conversion may have been due to increased average kinetic energy of the reactant species, i.e., propane and lattice oxygen, and $CO_2$ re-oxidation of the reduced vanadium species. At 650° C., the $VO_x$ on $\theta$-$Al_2O_3$ catalyst showed lower conversion, i.e., approx. 83%, likely due to side reactions occurring at higher temperature. However, the selectivity and yield of olefins increased consistently with temperature.

The incorporation of magnesium into $VO_x$ on $\theta$-$Al_2O_3$, i.e., making $VO_x$ on $\theta$-$Al_2O_3$/MgO (VM), can provide catalysts with a similar trends in propane conversion, olefin selectivity, and olefin yield relative to the reaction temperature. For instance, propylene conversion with an exemplary $VO_x$ on $\theta$-$Al_2O_3$/MgO (VM) catalyst was approx. 94% at 600° C., which dropped to approx. 91% at 625° C., and increased to approx. 97% at 650° C.

Examples

Catalyst Preparation: $VO_x$ on mixed support catalyst species were prepared by impregnating vanadyl acetyl acetate on a support having a 1:1 molar ratio of $\theta$-$Al_2O_3$ and alkaline earth metal oxide (MgO, CaO, or BaO). In all cases, oxides of MgO, CaO or BaO were utilized for the catalyst synthesis. In a typical support modification, 10 g of $\theta$-$Al_2O_3$ was combined with 3.953 g of MgO to obtain the desired 1:1 molar ratio of $\theta$-$Al_2O_3$:MgO support. A commercial $\theta$-$Al_2O_3$ from Inframat may be used, for example. The exact amount of vanadyl acetyl acetate precursor, i.e., $VO(acac)_2$, 265.157 g/mol, corresponding to 10 wt. % $V_2O_5$ (181.88 g/mol, 3.36 g/mL) was dissolved in toluene (0.867 g/mL), for example, 1.15 mL (1 g) of toluene to 72.9 mg of $VO(acac)_2$. Thereafter, the $\theta$-$Al_2O_3$ and alkaline earth metal oxide supports were introduced into the toluene solution, and the resulting mixture was left under constant stirring for 24. The alkaline earth metal oxide and O—$Al_2O_3$ were combined via excessive solvent impregnation. The resulting mixture, post-stirring, was filtered, and the solid was washed with copious amounts of fresh solvent. The filtered-off solid samples were then dried at 150° C. for 12 hour before calcination under a gas chromatography (GC) quality air stream for a period of 6 hours at 600° C.

The exemplary catalyst systems prepared are occasionally designated herein as V, VC, VB, and VM, wherein V means vanadium oxide(s) impregnated $\theta$-$Al_2O_3$, i.e., V/$\theta$-$Al_2O_3$, VC means vanadium oxide(s) impregnated on mixed $\theta$-$Al_2O_3$/CaO support, VB means vanadium oxide(s) impregnated on mixed $\theta$-$Al_2O_3$/BaO support, and VM is vanadium impregnated on mixed $\theta$-$Al_2O_3$/MgO support.

Catalyst Characterization

Figure 2:
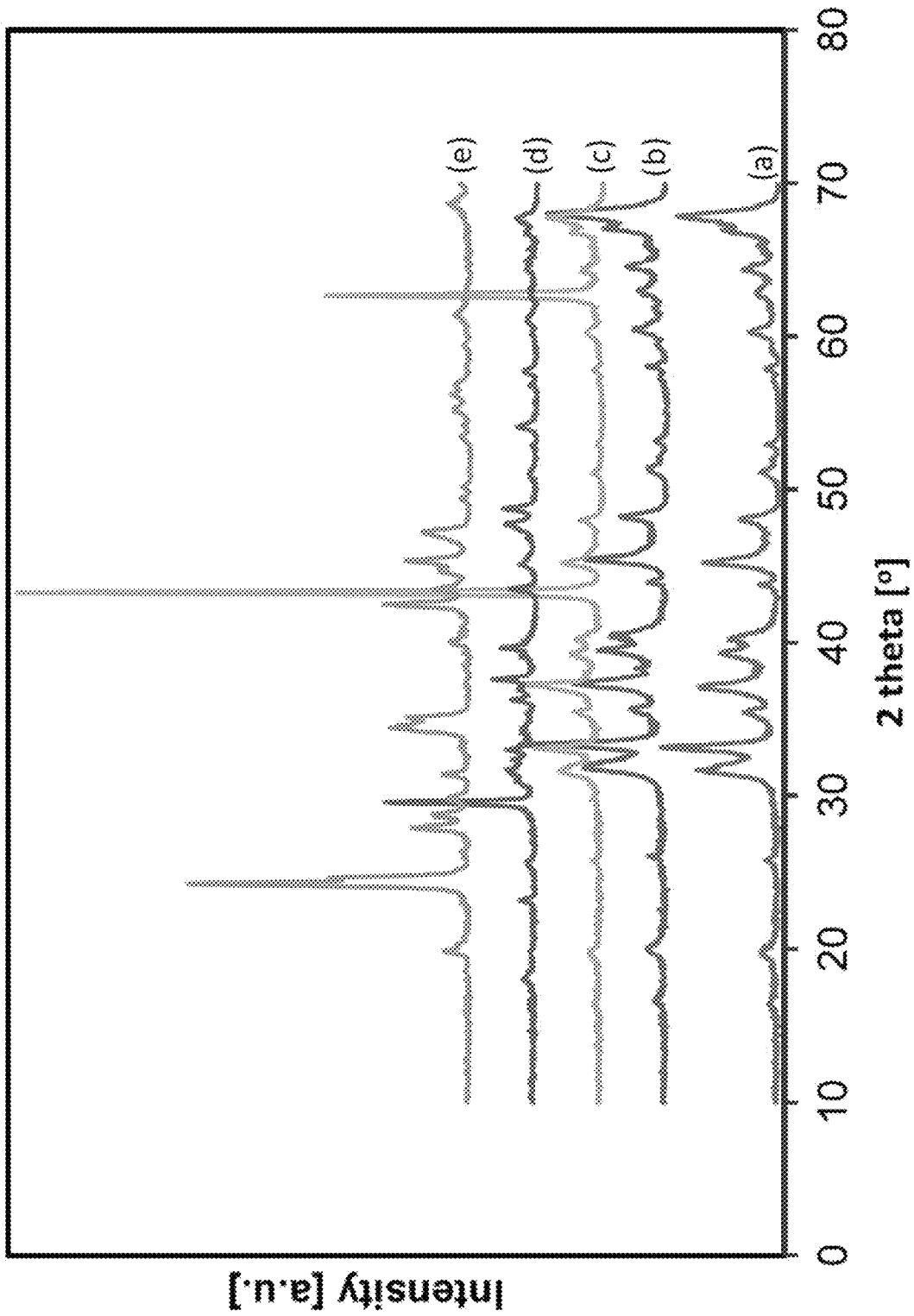
FIG. 2 shows x-ray diffraction (XRD) patterns of exemplary catalyst and/or support systems, i.e., $\theta$-$Al_2O_3$ (a), vanadium oxide—$VO_x$—on $\theta$-$Al_2O_3$ (b), $VO_x$ on $\theta$-$Al_2O_3$/MgO (c) $VO_x$ on $\theta$-$Al_2O_3$/CaO (d), and $VO_x$ on $\theta$-$Al_2O_3$/BaO (e)

X-Ray diffraction (XRD): The XRD patterns of exemplary $VO_x$ on $\theta$-$Al_2O_3$ (V), $VO_x$ on $\theta$-$Al_2O_3$/BaO (VB), $VO_x$ on $\theta$-$Al_2O_3$/CaO (VC), and $VO_x$ on $\theta$-$Al_2O_3$/MgO (VM) catalyst systems prepared as described above were analyzed using a Rigaku MiniFlex diffractometer machine. Samples were measured in the 2θ range of 10 to 75° using a step size of 0.02°. The results are shown in FIG. 2, discussed below.

Nitrogen ($N_2$) adsorption isotherms: To determine the BET surface areas and pore volumes of the synthesized catalysts and support, $N_2$ adsorption tests were conducted using a Micromeritics model ASAP 2010 analyzer. During the course of analysis, around 0.2 g of prepared catalyst was pretreated for 3 hours at 350° C. under the flow of nitrogen gas. Thereafter, $N_2$ adsorption was carried out in liquid nitrogen at 77 K and a relative pressure range of $10^{-6}$ to 1.

Temperature programmed reduction (TPR): TPR experiments of exemplary catalyst systems were conducted on freshly prepared catalyst samples by first pretreating the samples under the flow of argon (50 mL/min) for 3 hours at 300° C. Subsequently, the pretreated samples were cooled under Ar gas to room temperature. Following this, the cooled samples were treated with a 10.2% $H_2$—Ar mixture at a flow rate of 50 mL/min while simultaneously heating the whole system from ambient temperature at rate of 10° C./min to 800° C. Lastly, the volumes of $H_2$ consumed were measured using a thermal conductivity detector (TCD).

Temperature programmed desorption (TPD): Ammonia temperature program desorption ($NH_3$-TPD) was employed to probe acidic strength of the exemplary metal-supported catalyst systems. $NH_3$-TPD analysis was conducted as described in J. Ind. Eng. Chem. 2018, 64, 467-477, which is incorporated by reference herein in its entirety. In a typical analysis, about 0.28 g of freshly prepared catalyst sample were placed in a quartz tube and degassed under helium flow (30 mL/min for 2 hours at 500° C.) and then cooled to 100° C. Thereafter, a gaseous stream containing 4.55% of $NH_3$ in helium was introduced at a flow rate of 50 mL/min for 1 hour. After the ammonia loading, excessive physisorbed $NH_3$ molecules were removed by purging with pure helium gas for 1 hour. Finally, the desorbed $NH_3$ was recorded using a TCD ramping the system temperature at 10° C./min to 800° C.

The ODH experiments were conducted using fixed amounts of catalyst. Prior to purging the reactor basket and the vacuum box, an initial leak test was conducted. After the leak test, the reactor was heated in an oxygen free environment, e.g., in an argon gas environment, to the desired temperature. After attaining the desired temperature, the vacuum pump was then evacuated to 20.7 kPa (3.75 psi) to prepare the set up for the reaction. At this point, the catalyst was then fluidized by the impeller and an ethane feed was injected into the reactor by using a leak free syringe. After fluidization, the reaction was conducted for a specified time. After completion of the reaction, the isolation valve linking the reactor and vacuum box opened automatically. The products and all the un-reacted feed was taken into the vacuum box for analyzed using an online Agilent 7890A gas chromatograph (GC) equipped with a thermal conductivity detector (TCD) and flame ionization detector (FID) detector. Product analysis for each reaction was run three times to ensure accuracy. Finally, feed conversion and product selectivity were calculated based on integrated GC data using Equation 1 (propane conversion) and Equation 2 (product selectivity), below:

$$X_{C_3H_8}(\%) = \frac{\sum_j z_j n_j}{3n_{propane} + \sum_j z_j n_j} \times 100, \text{ and} \quad \text{Eq. 1}$$

$$S_j(\%) = \frac{z_j n_j}{\sum_j z_j n_j} \times 100, \quad \text{Eq. 2}$$

wherein $z_j$ means the number of atoms of carbon containing product j, $n_j$ means moles of gaseous carbon containing product j, and $n_{propane}$ means moles of unconverted propane in the product stream.

To better understand the morphology and nature of inventive catalyst systems, X-ray analysis, XPS analysis, and Raman spectroscopy were conducted, as discussed below regarding FIG. 2 and FIG. 3.

Nitrogen ($N_2$) Sorption Properties of Exemplary Catalyst Systems

Table 1, below, shows the $N_2$ sorption properties of the prepared catalyst systems. The surface areas and pore volumes of catalyst systems are dependent on the initial surface area of constituent support. As shown in Table 1, $\theta$-$Al_2O_3$ has a surface area of 77 m²/g. The support modifiers may be alkaline earth metal oxide modifiers (i.e., Mg, Ca, Ba) belonging to Group IIA of the periodic table. The decrease in the BET surface area ($S_{BET}$) of the catalysts as shown in Table 1, appears to follow the atomic diameter of the doping/modifying species, which increases in the order Mg<Ca<Ba.

TABLE 1

$N_2$ sorption properties of prepared catalyst systems.

| Samples | $S_{BET}$[m²/g] | $S_{Ext}$[m²/g] | $S_{Micro}$ [m²/g] | $V_M$ [cm³/g] | $V_T$ [cm³/g] |
|---|---|---|---|---|---|
| $\theta$-$Al_2O_3$ | 77 | 66 | 11 | 0.0045 | 0.317 |
| V | 75 | 67 | 8 | 0.0032 | 0.325 |
| VM | 48 | 42 | 6 | 0.0023 | 0.167 |
| VC | 39 | 33 | 6 | 0.0025 | 0.138 |
| VB | 19 | 15 | 4 | 0.0019 | 0.108 |

In Table 1, $S_{BET}$ corresponds to the Brunauer-Emmett-Teller (BET) surface area, $S_{Ext}$ corresponds to the external surface area, $S_{Micro}$ corresponds to the micropore surface area, $V_M$ corresponds to micropore volume, and $V_T$ corresponds to total pore volume.

The two prevalent side reaction during the oxidative dehydrogenation (ODH) of alkanes, especially the higher alkanes, are cracking and over oxidation (or combustion). Selectivity to paraffins (ethane and methane) and selectivity to $CO_x$ are the indicators of the extent of cracking or over oxidization during the ODH of propane. Generally, inventive catalyst systems exhibited low selectivity to $CO_x$, indicating that the combustion side reaction was suppressed. The low selectivity to $CO_x$ was most prevalent in the exemplary $VO_N$ on $\theta$-$Al_2O_3$/CaO (VC) catalyst, which exhibited only ~2% selectivity to $CO_x$ at 650° C. Furthermore, each catalyst system showed preference to the type of olefin generated during the oxidative dehydrogenation (ODH) process. The higher LT:HT acidity ratio in the exemplary $VO_x$ on $\theta$-$Al_2O_3$/BaO (VB) catalyst explain its superior performance.

Referring now to the drawings, wherein like reference numerals designate identical or corresponding parts throughout the several views.

ODH of Propane Using a Fluidized CREC Riser Simulator

Figure 1E:
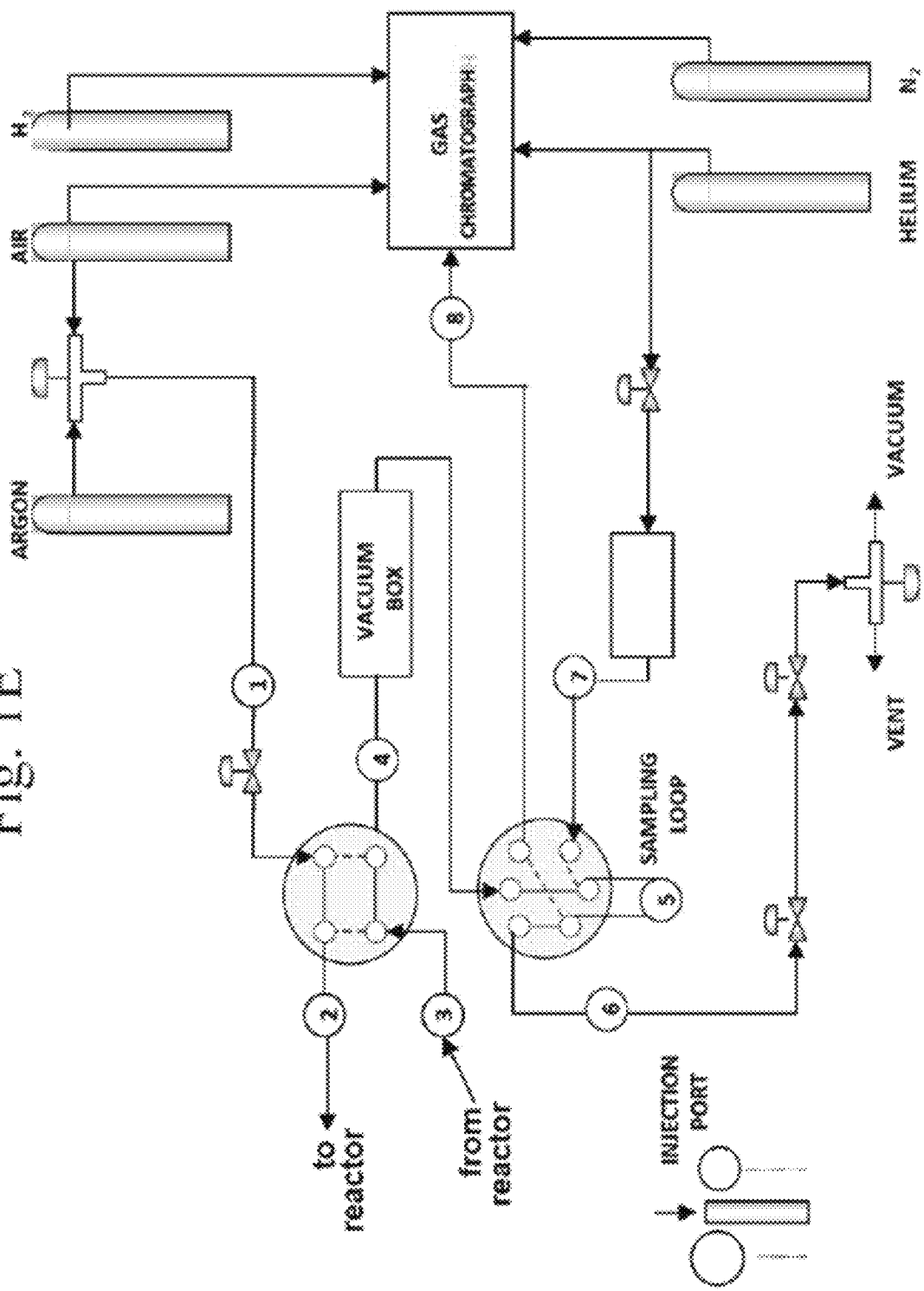
FIG. 1E shows a representative schematic diagram of the CREC Riser Simulator experimental set-up used to study the inventive catalysts.

A 3D diagram of the CREC-Riser simulator reactor body is as shown in FIG. 1A to 1D, while FIG. 1E shows the schematic diagram of the CREC Riser Simulator experimental set-up including the GC analysis. The oxidative dehydrogenation (ODH) catalytic activity of the $VO_x$ on $\theta$-$Al_2O_3$ (V), $VO_x$ on $\theta$-$Al_2O_3$/MgO (VM), $VO_x$ on $\theta$-$Al_2O_3$/CaO (VC), and $VO_x$ on $\theta$-$Al_2O_3$/BaO (VB) catalyst systems were evaluated using a fluidized CREC Riser Simulator. Details on the fluidized bed CREC reactor are described in *Ind. Eng. Chem. Res.* 2018, 57(9), 3128-3137, which is incorporated by reference herein in its entirety. The fluidized bed reactor, with a capacity of 53 mL, is a batch unit that mimics fluidized bed reactor operational conditions. The CREC riser simulator includes a lower (15b) and upper (15a) shell or reactor, which aids loading and removal of catalyst samples into reactor chamber. The upper shell or reactor (15a) comprises an impeller (10) with a rotational speed of up to 7000 RPM, through the cooling jacket (11) with an internal packing gland (18), which impeller (10) facilitates fluidization of catalyst in the reactor's basket (25) located in the lower shell (15b). The impeller (10) extends vertically downwardly into the upper reaction chamber (15a), through a cooling jacket (11) with has a cooling jacket nipple or feed (12). An injector or syringe (14) may extend generally horizontally into the lower reactor space (15b) through a injector cooling jacket (13), and a spare injector (17) may be included on the side. A thermocouple (16) may extend horizontally through the upper (15a) and lower (15b) reactor spaces into the catalyst basket (25), which basket (25) may contain an upper retaining ring (20), an upper grid (21), a (catalyst) basket body (22), a lower grid (23), and a lower retaining ring (24).

Chemical Composition of Exemplary Catalyst Systems

FIG. 2 presents x-ray diffraction (XRD) patterns of pure $\theta$-$Al_2O_3$ support, $VO_x$ on $\theta$-$Al_2O_3$ (V), $VO_x$ on $\theta$-$Al_2O_3$/MgO (VM), $VO_x$ on $\theta$-$Al_2O_3$/CaO (VC), and $VO_x$ on $\theta$-$Al_2O_3$/BaO (VB). The addition of $VO_x$ species to the bare $\theta$-$Al_2O_3$ support, i.e., sample V, indicates a reduction in the peak intensities of the support. No $VO_x$ species peak was observed after impregnation with vanadium precursor. The absence of $VO_x$ species peaks implies that any $VO_x$ species formed were unidentifiable by x-ray. Also, the XRD pattern of the exemplary VM catalyst system showed peaks of $\theta$-$Al_2O_3$ and MgO supports, but no peaks corresponding to vanadium species.

In the XRD pattern of samples VB and VC, not only peaks corresponding to BaO and CaO species were found, but also peaks corresponding to their respective carbonates, i.e., BaCO$_3$ and CaCO$_3$. The XRD patterns of exemplary catalysts were matched using PDXL software. For the VB sample, the constituent phases of θ-Al$_2$O$_3$, BaCO$_3$, and BaO matched with PDF database references 01-086-1410 (θ-Al$_2$O$_3$), 01-078-4342 (BaCO$_3$), and 01-085-0418 (BaO). The weight percentage contents in VB were 50 wt. % θ-Al$_2$O$_3$, 43 wt. % BaCO$_3$ and 7 wt. % BaO in VB. In the case of VC, the constituent phases θ-Al$_2$O$_3$, CaCO$_3$, and CaO matched with PDF database references 01-086-1410 (θ-Al$_2$O$_3$), 01-070-5490 (CaCO$_3$), and 01-085-0849 (CaO). The weight percentage contents in VC were 67 wt. % of θ-Al$_2$O$_3$, 26 wt. % CaCO$_3$, and 7 wt. % CaO.

Figure 3:
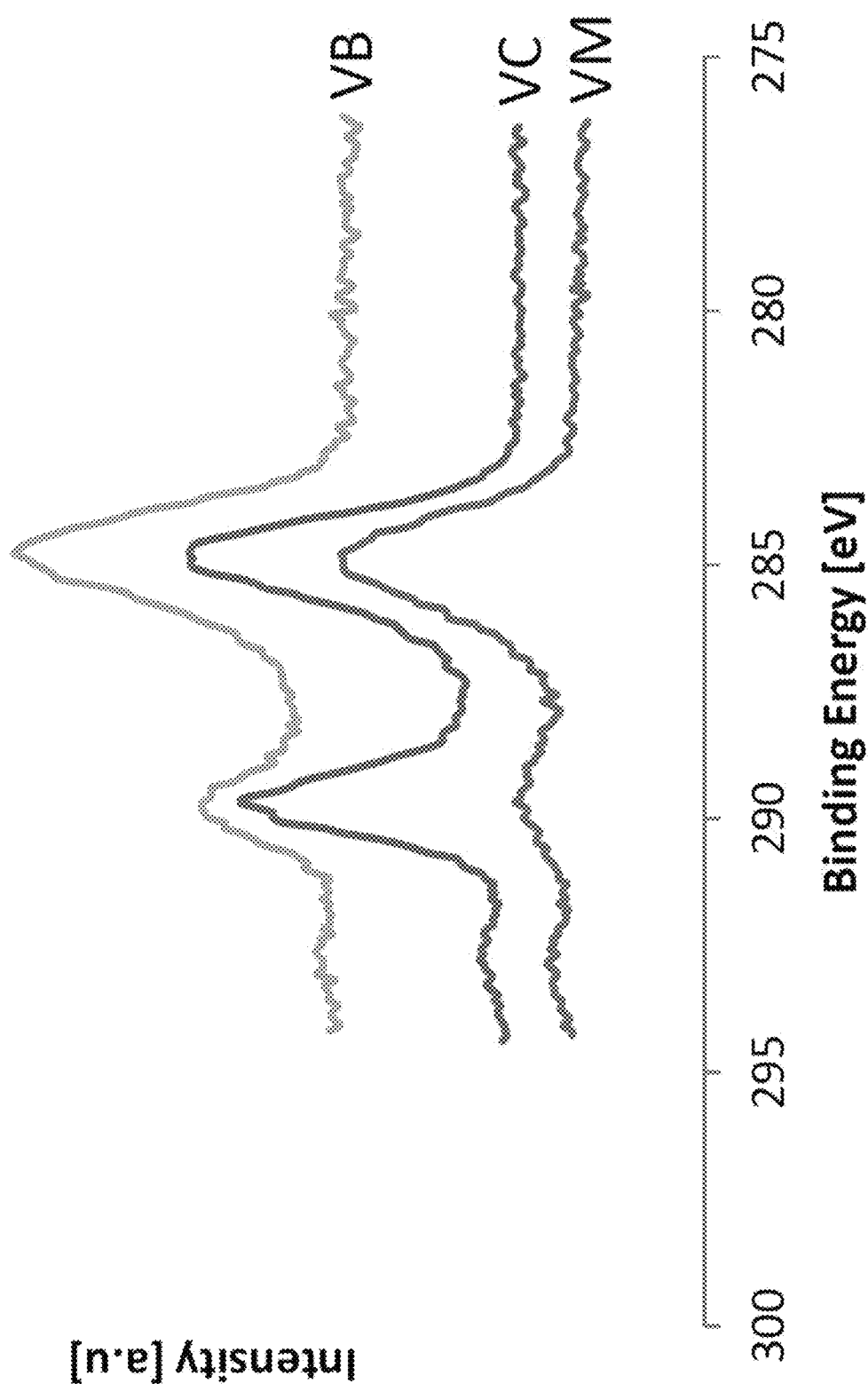
FIG. 3 shows x-ray photoelectron spectroscopy (XPS) spectra of exemplary inventive catalyst systems, i.e., $VO_x$ on $\theta$-$Al_2O_3$/MgO ("VB") $VO_x$ on $\theta$-$Al_2O_3$/CaO ("VC"), and $VO_x$ on $\theta$-$Al_2O_3$/BaO ("VB")
Figure 4:
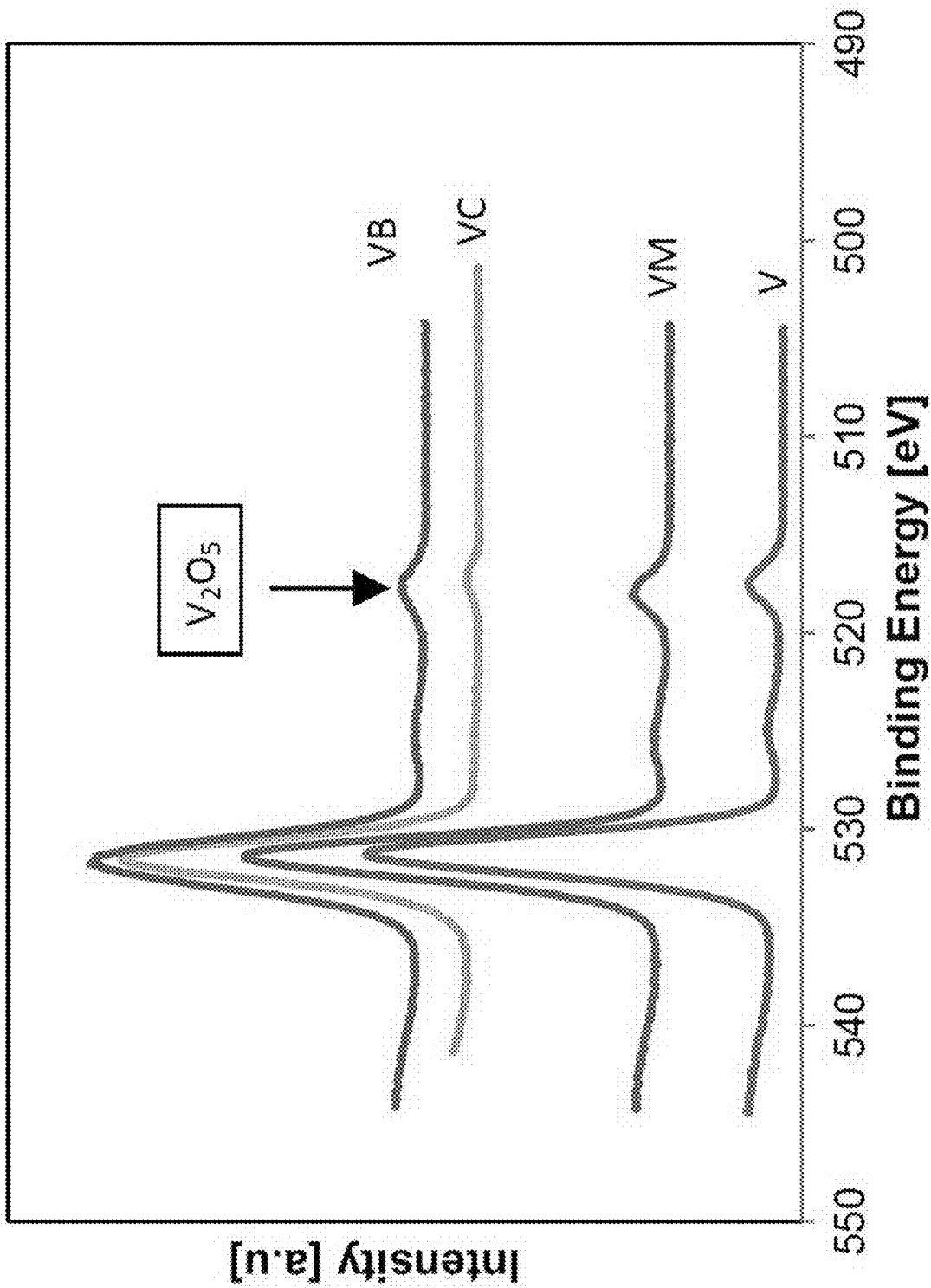
FIG. 4 shows XPS spectra identifying $V_2O_5$ vanadium species in exemplary inventive catalyst systems $VO_x$ on $\theta$-$Al_2O_3$ (V), $VO_x$ on $\theta$-$Al_2O_3$/MgO (VM), $VO_x$ on $\theta$-$Al_2O_3$/CaO (VC), and $VO_x$ on $\theta$-$Al_2O_3$/BaO (VB)

FIG. 3 shows x-ray photoelectron spectroscopy (XPS) plots for carbon in θ-Al$_2$O$_3$/MgO (VM), VO$_x$ on θ-Al$_2$O$_3$/CaO (VC), and VO$_x$ on θ-Al$_2$O$_3$/BaO (VB) clearly show two distinct peaks of C. XPS analysis of exemplary catalyst further indicated the presence of carbonate species in the VB and VM samples. The first peak, at 284.8 eV, relates to the inherent adventitious carbon peak, while the peak at ~290 eV corresponds to carbonate species present in VM, VC, and VB. The starting materials for synthesis of VB, VC, and VM were BaO, CaO, and MgO mixed in equimolar ratio with alumina. However, during the synthesis, the acetate ion from the vanadium acetylacetonate precursor used during sample preparation may oxidize to CO$_2$. This CO$_2$, possibly coupled with atmospheric CO$_2$, then reacts with the alkaline earth metal oxides to form the respective carbonates. In the VM sample, the MgCO$_3$ formed appears to have reverted to MgO during calcination, possibly by off-gassing CO$_2$. In the VB and VC samples, the BaCO$_3$ and CaCO$_3$ formed appear to remain stable even after calcination at 550° C. The vanadium species present in exemplary catalyst systems synthesized were not identifiable by XRD analysis, but XPS analysis indicates the presence of vanadium species. The XPS plots in FIG. 4 shows the presence of V$_2$O$_5$ species in the exemplary catalysts, as indicated by V$_{2p}$ peaks at approximately 517 eV.

Acidity of Exemplary Catalyst Systems

Figure 5:
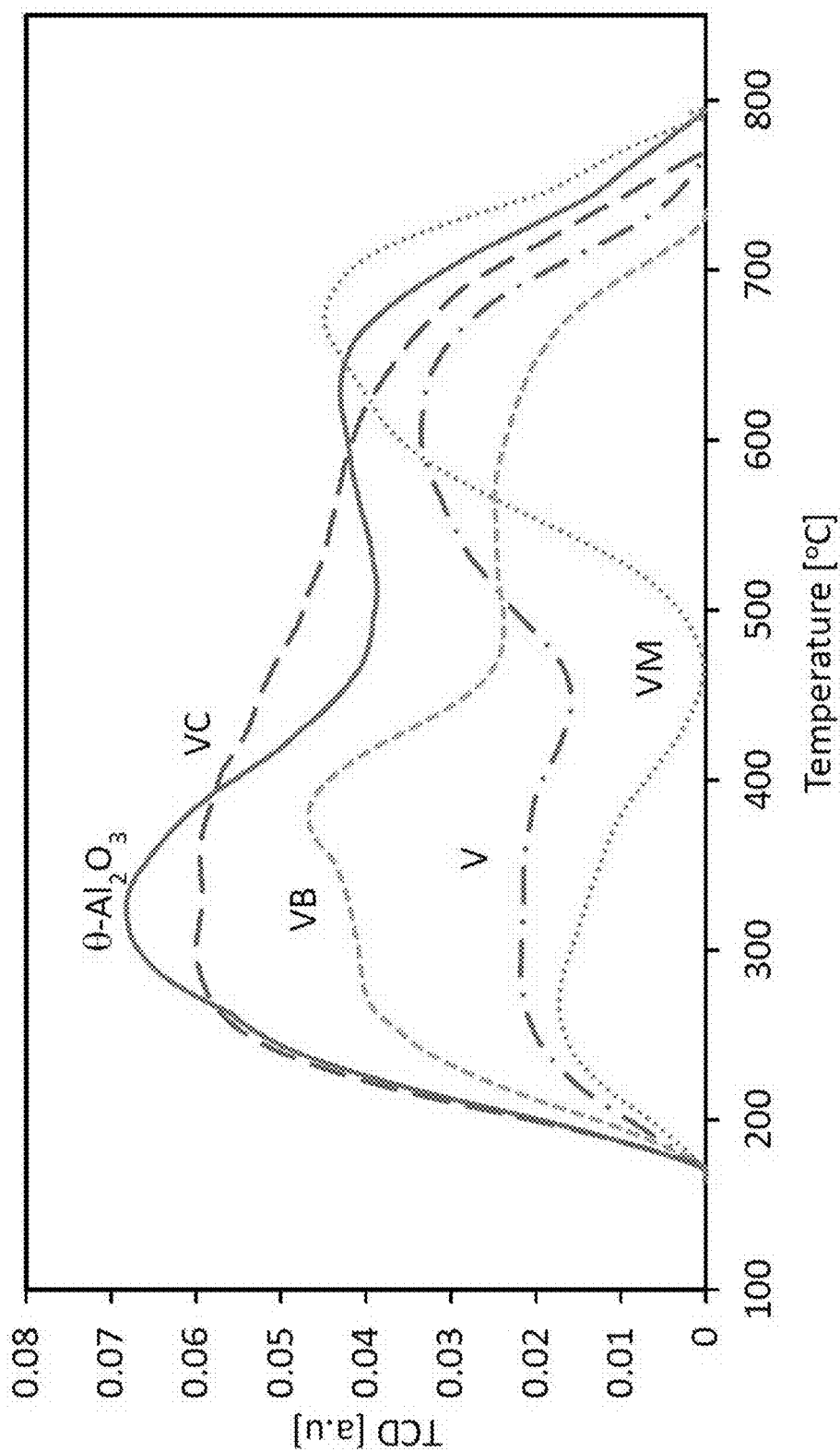
FIG. 5 shows ammonia $NH_3$ temperature programmed desorption (TPD, or thermal desorption spectroscopy, TDS) profiles of exemplary inventive catalyst systems $VO_x$ on $\theta$-$Al_2O_3$ (V), $VO_x$ on $\theta$-$Al_2O_3$/MgO (VM), $VO_x$ on $\theta$-$Al_2O_3$/CaO (VC), and $VO_x$ on $\theta$-$Al_2O_3$/BaO (VB)

FIG. 5 shows the NH$_3$-TPD, i.e., temperature programmed desorption, also referred to as thermal desorption spectroscopy (TDS), profiles of plain, undoped θ-Al$_2$O$_3$ support and the exemplary mixed-support catalyst samples and values from the experiment are shown below in Table 2. The order of acidity of the samples was found to be θ-Al$_2$O$_3$>VO$_x$ on θ-Al$_2$O$_3$/CaO (VC)>VO$_x$ on θ-Al$_2$O$_3$/BaO (VB)>VO$_x$ on θ-Al$_2$O$_3$/MgO (VM)>VO$_x$ on θ-Al$_2$O$_3$ (V). The acidity distribution differed in each catalyst system, with θ-Al$_2$O$_3$ having primarily two peaks, a first peak at low temperature corresponding to weak/medium acid sites and a second peak at higher temperature corresponding to strong acid sites. After incorporating vanadium into θ-Al$_2$O$_3$ (sample "V," i.e., VO$_x$ on θ-Al$_2$O$_3$), an apparent reduction in these peaks was observed. This reduction of acidity may have resulted from neutralization of some acidic sites by VO$_x$ species and/or the blocking of θ-Al$_2$O$_3$ pores by VO$_x$ species, thereby preventing access to some acid sites in θ-Al$_2$O$_3$ support.

Furthermore, the acidity in VO$_x$ on θ-Al$_2$O$_3$/CaO (VC), VO$_x$ on θ-Al$_2$O$_3$/BaO (VB), and VO$_x$ on θ-Al$_2$O$_3$/MgO (VM) appears to operate as a function of contributory effects from both θ-Al$_2$O$_3$ and alkaline earth metal oxide. For instance, in the exemplary VO$_x$ on θ-Al$_2$O$_3$/CaO (VC) catalyst, the temperature programmed desorption (TPD) peak appeared to be a broadening type, or merging of two peaks, as opposed to two distinct peaks as seen for the pure θ-Al$_2$O$_3$ support. This broadening indicates the presence of mainly medium strength acidic sites in the VO$_x$ on θ-Al$_2$O$_3$/CaO (VC) sample. Furthermore, the VO$_x$ on θ-Al$_2$O$_3$/BaO (VB) sample showed three peaks, which may be classified as weak, medium, and strong acidities. The VO$_x$ on θ-Al$_2$O$_3$/MgO (VM) sample showed two main peaks, a first peak at low temperature, corresponding to weak-medium acidity, and a second peak at high temperature, corresponding to strong acidity. The VO$_x$ on θ-Al$_2$O$_3$/MgO (VM) sample was observed to have the strongest acid sites as the peak at higher temperature in VM had the highest centering temperature as evident in FIG. 5.

TABLE 2

Acidity of catalyst systems.

| Samples | NH$_3$ Desorbed at LT$^a$ [mmol/g] | NH$_3$ Desorbed at HT$^b$ [mmol/g] | Total NH$_3$ Desorbed [mmol/g] | LT/HT |
|---|---|---|---|---|
| θ-Al$_2$O$_3$ | 0.710 | 0.61 | 1.32 | 1.16 |
| V | 0.178 | 0.28 | 0.45 | 0.64 |
| VM | 0.139 | 0.42 | 0.56 | 0.33 |
| VC | 0.634 | 0.57 | 1.20 | 1.11 |
| VB | 0.443 | 0.28 | 0.72 | 1.58 |

$^a$LT: Low temperature;
$^b$HT: High temperature wherein LT ranges from 180 to 470° C., while HT range from 470 to 800° C.

FIG. 6A to 6D show the temperature-programmed reduction (TPR) profiles of VO$_x$ on θ-Al$_2$O$_3$ (V), VO$_x$ on θ-Al$_2$O$_3$/MgO (VM), VO$_x$ on θ-Al$_2$O$_3$/CaO (VC), and VO$_x$ on θ-Al$_2$O$_3$/BaO (VB).

Figure 6A:
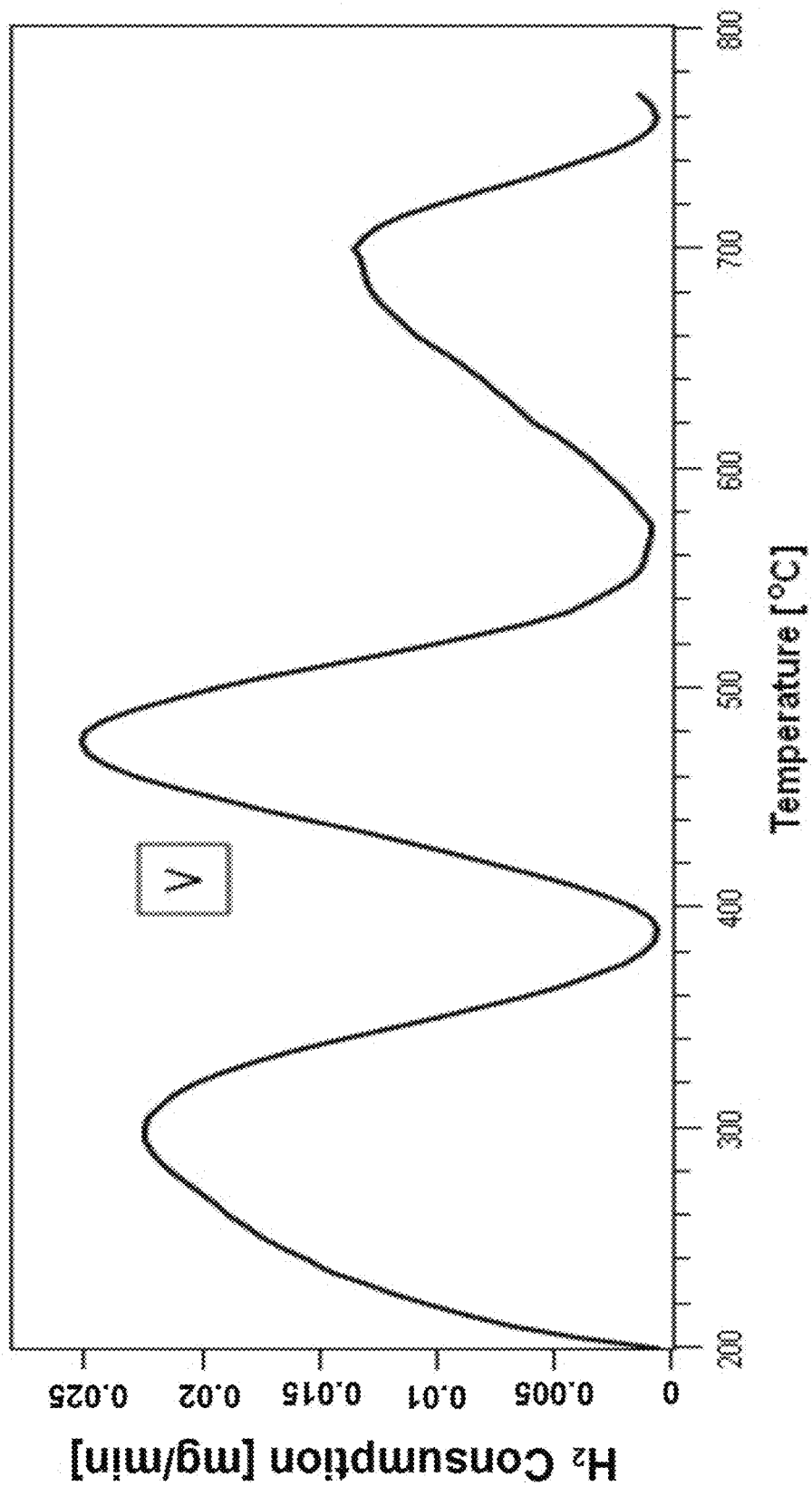
FIG. 6A shows a temperature programmed reduction (TPR) profile of an exemplary $VO_x$ on $\theta$-$Al_2O_3$ (V) catalyst system.

The TPR profile in FIG. 6A indicates a multi-stage reduction of V$_2$O$_5$ to V$_2$O$_3$. Low temperature peaks are typically ascribed to the reduction of isolated monomeric units, while the high temperature peak(s) are attributed to reduction of oligomeric units, and peaks which have temperature maximum around 700° C. are associated with the presence of V$_2$O$_5$ bulk-like species. The exemplary VO$_x$ on θ-Al$_2$O$_3$ (V) catalyst showed three peaks with peak maxima at approximately 298, 476, and 699° C.

Figure 6B:
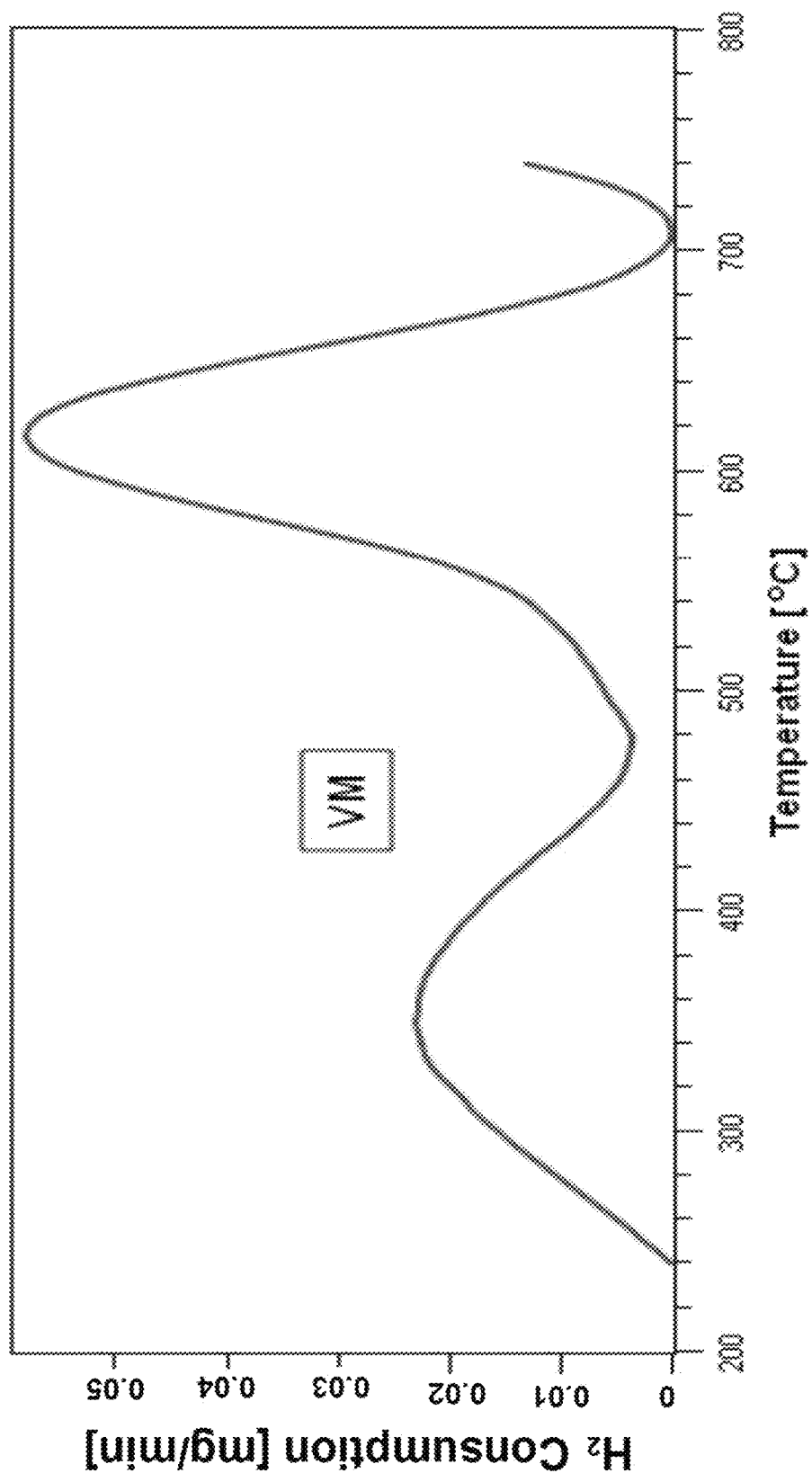
FIG. 6B shows a temperature programmed reduction (TPR) profile of an exemplary inventive $VO_x$ on $\theta$-$Al_2O_3$/MgO (VM) catalyst system.
Figure 6C:
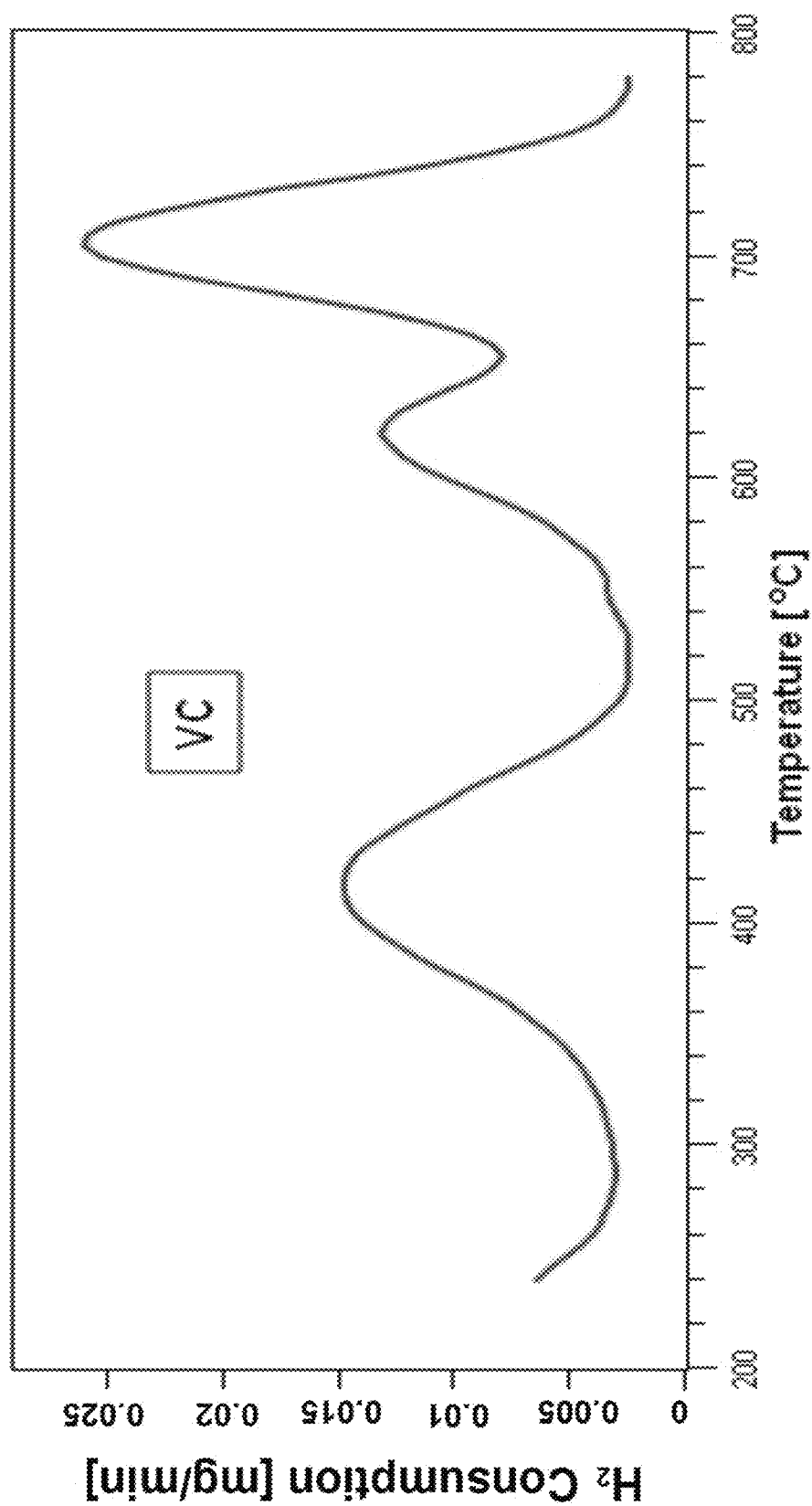
FIG. 6C shows a temperature programmed reduction (TPR) profile of an exemplary inventive $VO_x$ on $\theta$-$Al_2O_3$/CaO (VC) catalyst system.
Figure 6D:
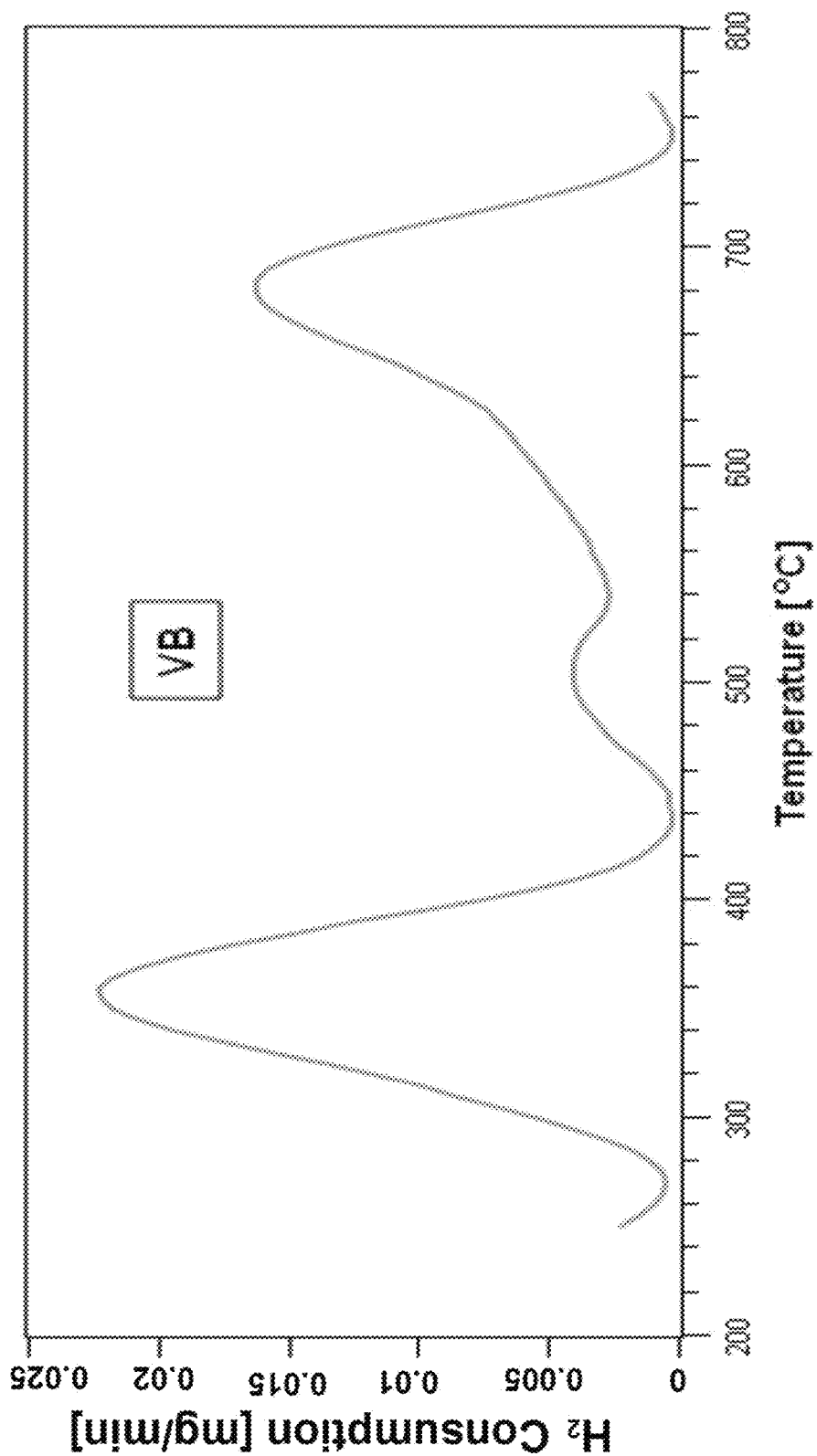
FIG. 6D shows a temperature programmed reduction (TPR) profile of an exemplary inventive $VO_x$ on $\theta$-$Al_2O_3$/BaO (VB) catalyst system.

As seen in FIG. 6B the exemplary VO$_x$ on θ-Al$_2$O$_3$/MgO (VM) catalyst was observed to have two peak maxima, at approximately 343 and 618° C. As seen in FIG. 6C, the VO$_x$ on θ-Al$_2$O$_3$/CaO (VC) sample can be observed to have peak maxima at approximately 414, 621, and 707° C. As seen in FIG. 6D, in the VO$_x$ on θ-Al$_2$O$_3$/BaO (VB) sample, peak maxima at approximately 358, 507, and 681° C. can be observed. From these peak maxima positions observed in samples prepared in the Examples it can be inferred that the samples contain vanadium species in the monomeric, oligomeric, and bulk states.

ODH of Propane Fluidized CREC Riser Simulator

Figure 7:
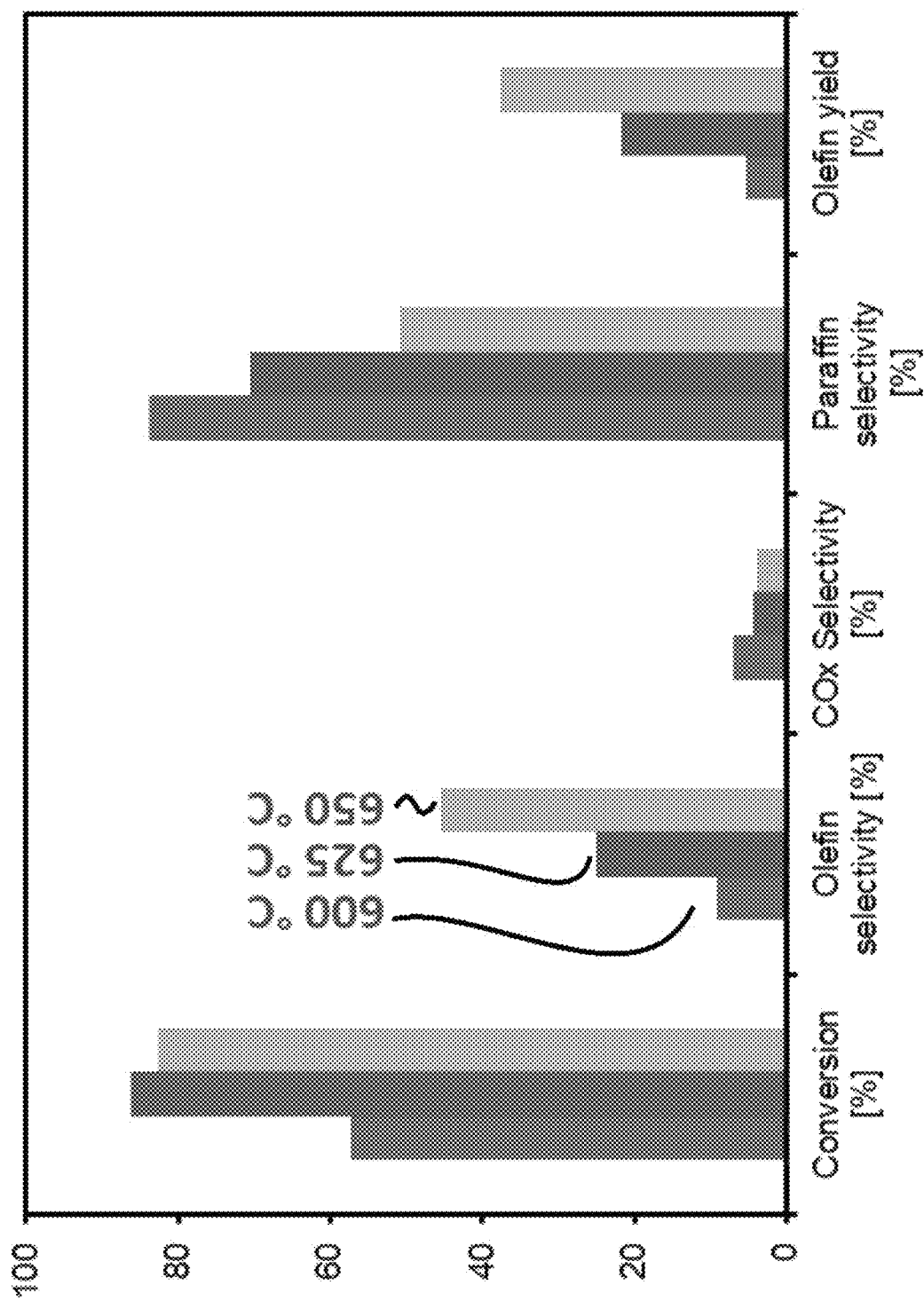
FIG. 7 shows catalytic activity of an exemplary $VO_x$ on $\theta$-$Al_2O_3$ (V) catalyst system in the oxidative dehydrogenation (ODH) of propane.

FIG. 7 shows the oxidative dehydrogenation (ODH) of propane over the VO$_x$ on θ-Al$_2$O$_3$ sample in the riser simulator shown in FIG. 1A to 1E. The initial reactor pressure is atmospheric (inert atmosphere); and a feed injection (1.2 mL of propane) was achieved using syringe and the reaction proceeded for 30 s; stirring was at an average of 4000 rpm although the impeller could go to a maximum of 7000 rpm. FIG. 7 illustrates that the conversion increased from 57% to 86% when the temperature was increased from 600 to 625° C. This conversion increase may be ascribed partly to the increase in the average kinetic energy of the reactant molecules, i.e., propane and lattice oxygen of the metal catalyst, to interact with the surface of the catalyst. Furthermore, a trend towards increased CO$_2$ re-oxidation of the reduced $VO_x$ species during the reaction period can be detected. At 650° C., the conversion was observed to decrease slightly, probably due to competing side reactions, which limit the extent of $CO_2$ re-oxidation of the reduced $VO_x$ species. This decrease in conversion, in turn, may have limited the total amount of available lattice oxygen from the various $VO_x$ species present in the V/θ-$Al_2O_3$ catalyst. Therefore, a reaction temperature of 625° C. seems to be an optimum for the ODH of propane over the V/θ-$Al_2O_3$ catalyst prepared herein. The olefin yield and selectivity increased with the reaction temperature, consistent with the reports on the effect of temperature on propane ODH in the art.

Figure 8:
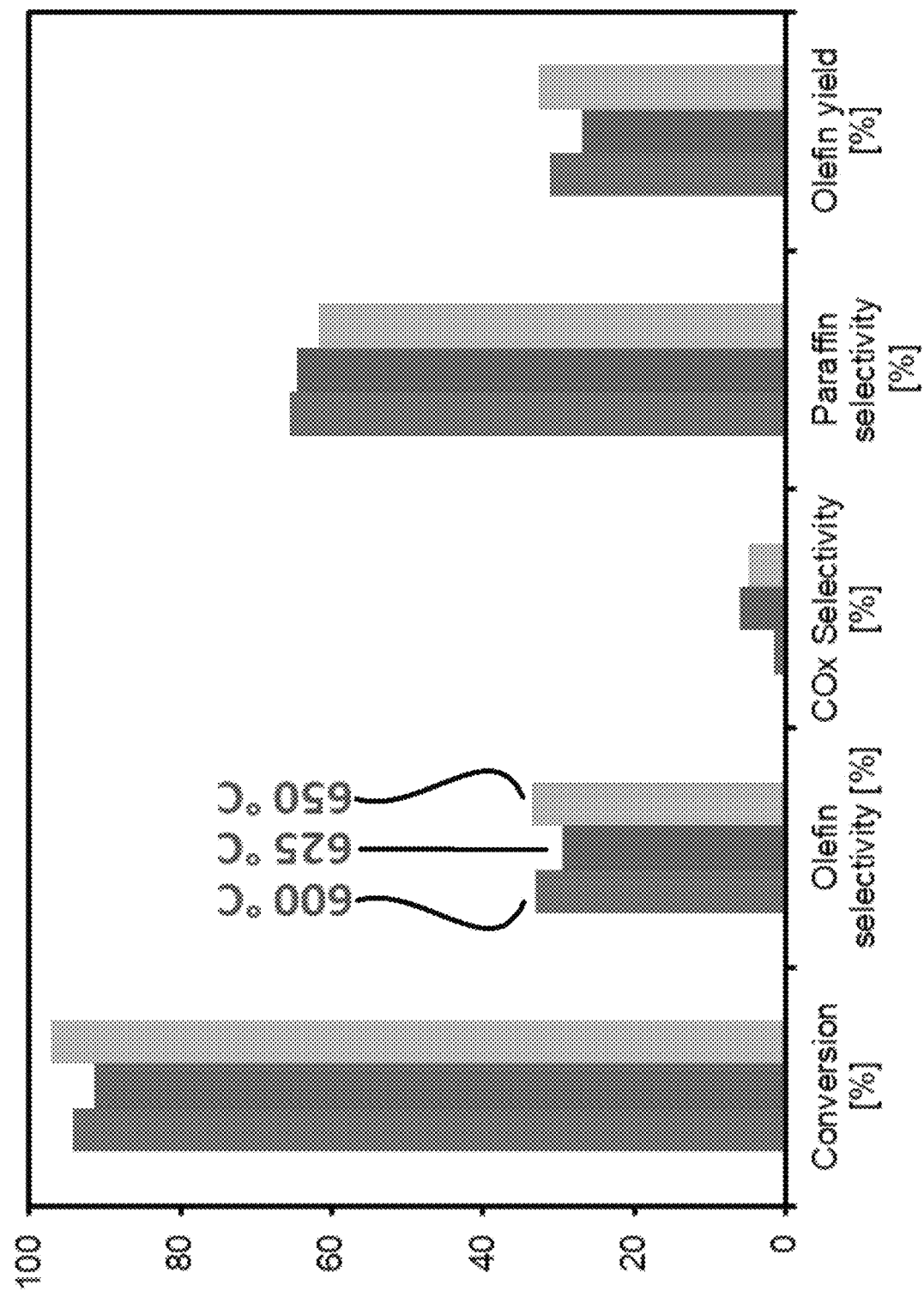
FIG. 8 shows catalytic activity of an exemplary inventive $VO_x$ on $\theta$-$Al_2O_3$/MgO (VM) catalyst system in the oxidative dehydrogenation (ODH) of propane.
Figure 9:
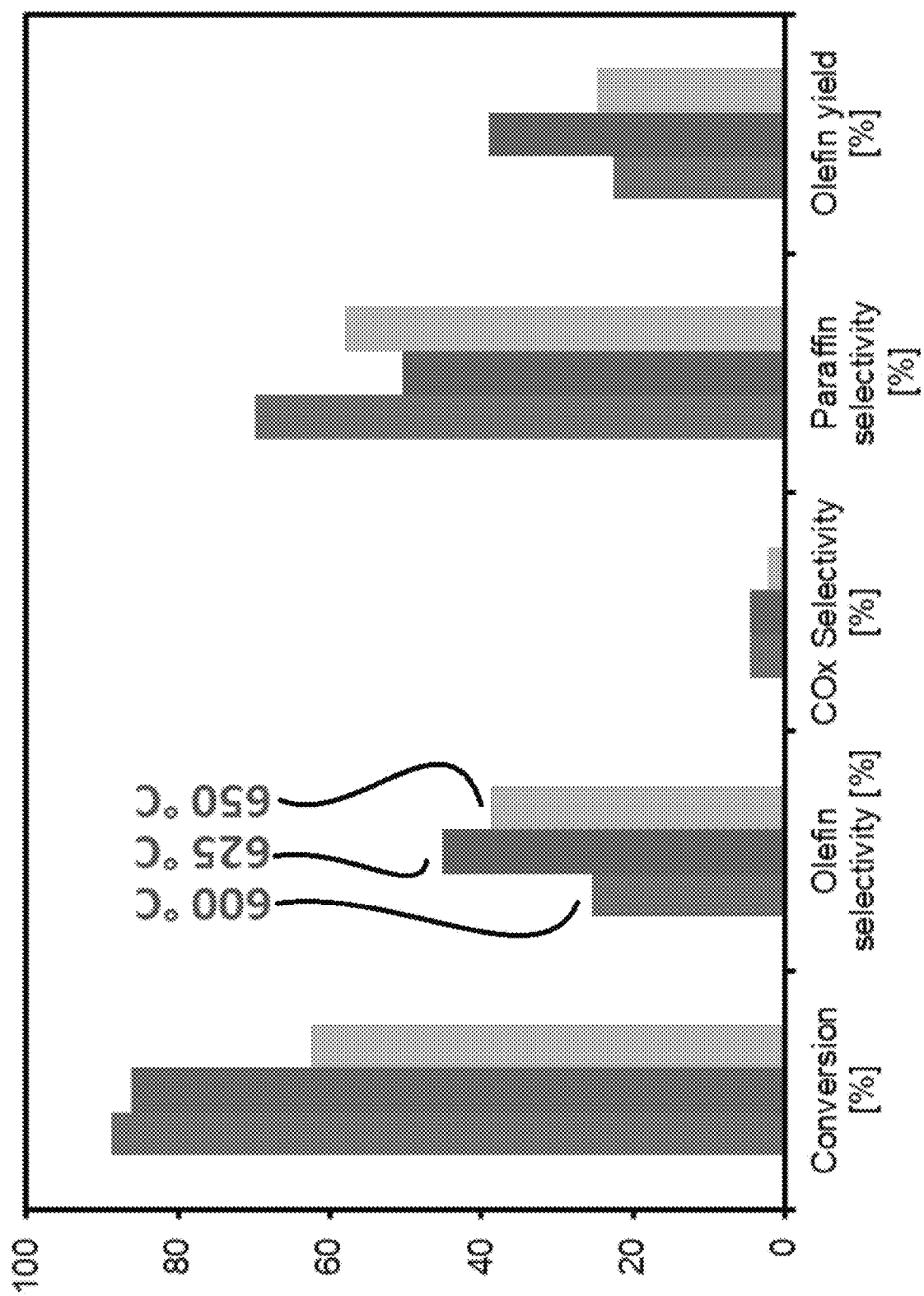
FIG. 9 shows catalytic activity of an exemplary inventive $VO_x$ on $\theta$-$Al_2O_3$/CaO (VC) catalyst system in the oxidative dehydrogenation (ODH) of propane.
Figure 10:
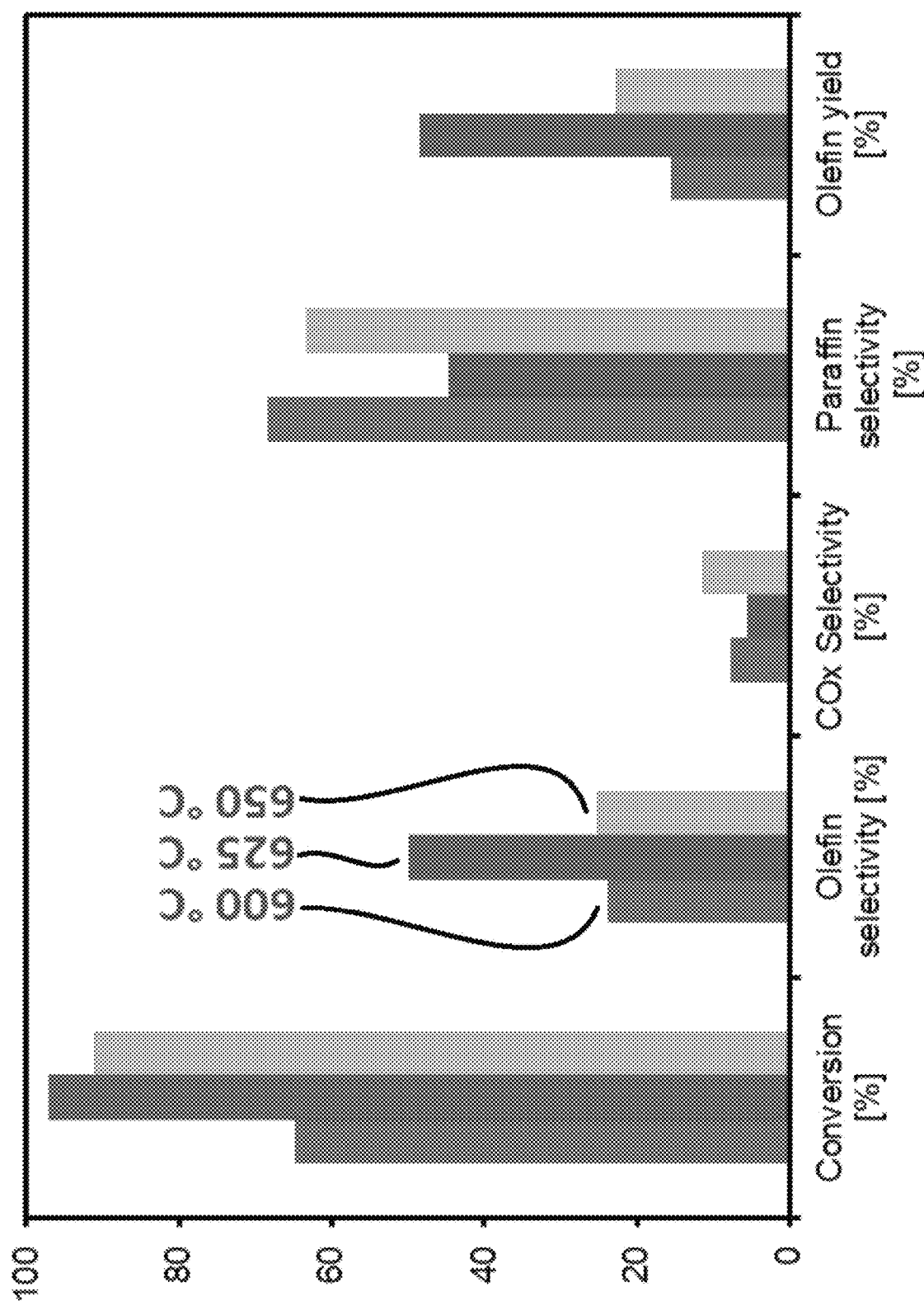
FIG. 10 shows catalytic activity of an exemplary inventive $VO_x$ on $\theta$-$Al_2O_3$/BaO (VB) catalyst system in the oxidative dehydrogenation (ODH) of propane.

FIGS. 8, 9, and 10 show the catalytic activity of the exemplary $VO_x$ on θ-$Al_2O_3$/MgO (VM, FIG. 8), $VO_x$ on θ-$Al_2O_3$/CaO (VC, FIG. 9), and $VO_x$ on θ-$Al_2O_3$/BaO (VB, FIG. 10) catalysts for the oxidative dehydrogenation (ODH) of propane. FIGS. 8 to 10 indicate that the activity of each catalyst varies at different studied temperature owing to the makeup of each catalyst system.

For the VM sample, in FIG. 8, propane conversion, olefin selectivity, and olefin yield can be observed to follow similar trends with respect to the reaction temperature. That is, each of these variables showed the highest values of conversion, selectivity for olefins, and yield at 650° C., and lowest values at 625° C. The trends for the VM sample indicated that the increase in the amount of reducible $VO_x$ species at 650° C. outweighs the excessive coking or possible re-oxidation of the olefins. Possibly, some reduced $VO_x$ species could have re-oxidized by abstracting an oxygen atom from $CO_2$ when the temperature was increased to 650° C., thereby enhancing propane conversion, olefin selectivity, and yield. The results for the exemplary $VO_x$ on θ-$Al_2O_3$/MgO (VM) catalyst are consistent with findings in the art that the reaction rate of propane ODH is dependent on the re-oxidation of reduced sites over $VO_x$ catalyst. For example, the conversion was ~94% at 600° C., dropping to ~91% at 625° C., and increasing to ~97% at 650° C., using $VO_x$ on θ-$Al_2O_3$/MgO (VM).

Numerous modifications and variations of the present invention are possible in light of the above teachings. It is therefore to be understood that within the scope of the appended claims, the invention may be practiced otherwise than as specifically described herein.

REFERENCE SIGNS 1 first pipe element
2 second pipe element
3 third pipe element
4 fourth pipe element
5 fifth pipe element
6 sixth pipe element
7 seventh pipe element
8 eighth pipe element
10 impeller
11 cooling jacket
12 cooling jacket nipple
13 injector cooling jacket
14 syringe/(manual) injector
15a upper reactor
15b lower reactor
16 thermocouple port
17 spare injector
18 packing gland
20 upper retaining ring
21 upper grid
22 (catalyst) basket body
23 lower grid
24 lower retaining ring
25 catalyst basket

The invention claimed is:

1. A catalyst, comprising:
   at least 65 wt. %, based on total catalyst weight, of a support material comprising, based on total support weight, at least 50 wt. % θ-alumina, 5 to 45 wt. % of an alkaline earth metal oxide, and at least 5 wt. % of an alkaline earth metal carbonate; and
   5 to 20 wt. %, based on the total catalyst weight, of a catalytic material comprising at least 90 wt. %, based on total catalytic material weight, of one or more vanadium oxides, disposed on the support material.

2. The catalyst of claim 1, wherein the alkaline earth metal oxide comprises magnesium oxide, calcium oxide, strontium oxide, and/or barium oxide.

3. The catalyst of claim 1, wherein the alkaline earth metal carbonate comprises magnesium carbonate, calcium carbonate, strontium carbonate, and/or barium carbonate.

4. The catalyst of claim 1, wherein the alkaline earth metal oxide comprises at least 90 wt. % calcium oxide, based on total alkaline earth metal oxide weight, and
   wherein the alkaline earth metal carbonate comprises at least 90 wt. % calcium carbonate.

5. The catalyst of claim 1, wherein the alkaline earth metal oxide comprises at least 90 wt. % barium oxide, based on total alkaline earth metal oxide weight, and
   wherein the alkaline earth metal carbonate comprises at least 90 wt. % barium carbonate.

6. The catalyst of claim 1, wherein the one or more vanadium oxides comprise an amount in a range of from 5 to 50 wt. % of $V_2O_5$, relative to total vanadium oxide weight.

7. The catalyst of claim 1, wherein the support material comprising at least 25 wt. % of the alkaline earth metal carbonate.

8. The catalyst of claim 1, wherein the catalytic material is up to 10 wt. % of the total catalyst weight, with a remainder of the catalyst weight being the support material.

9. The catalyst of claim 1, having a BET surface area in a range of from 15 to 60 $m^2/g$.

10. The catalyst of claim 1, having a total acidity in a range of 0.6 to 1.5 mmol of $NH_3$ per gram of catalyst.

11. The catalyst of claim 1, suitable to provide a higher olefin selectivity in oxidative dehydrogenation absent gaseous oxygen at 625° C. relative to 600 and 650° C.

12. The catalyst of claim 1, suitable to provide a higher olefin yield in oxidative dehydrogenation absent gaseous oxygen at 625° C. relative to 600 and 650° C.

13. The catalyst of claim 1, suitable to provide an olefin selectivity over 40% in oxidative dehydrogenation absent gaseous oxygen at 625° C.

14. The catalyst of claim 1, suitable to provide an olefin yield over 30% in oxidative dehydrogenation absent gaseous oxygen at 625° C.

15. The catalyst of claim 1, suitable to provide a selectivity to $CO_x$ of no more than 5% in oxidative dehydrogenation absent gaseous oxygen at 625° C.

16. The catalyst of claim 1, having a low temperature acidity measured at a temperature in a range of 180 to less than 470° C. in a range of 0.139 to 0.634 mmol of $NH_3$ per gram of catalyst.

17. The catalyst of claim 1, having a high temperature acidity measured at a temperature in a range of 470 to 800° C. in a range of 0.28 to 0.57 mmol of $NH_3$ per gram of catalyst.

18. The catalyst of claim 1, having a ratio of a low temperature acidity measured at a temperature in a range of 180 to less than 470° C. to a high temperature acidity measured at a temperature in a range of 470 to 800° C. in a range of 0.33 to 1.58.

19. The catalyst of claim 1, wherein the alkaline earth metal oxide and alkaline earth metal carbonate are crystalline by PXRD.

\* \* \* \* \*